United States Patent
Diolaiti et al.

(10) Patent No.: US 10,537,994 B2
(45) Date of Patent: *Jan. 21, 2020

(54) MEDICAL ROBOTIC SYSTEM PROVIDING SENSORY FEEDBACK INDICATING A DIFFERENCE BETWEEN A COMMANDED STATE AND A PREFERRED POSE OF AN ARTICULATED INSTRUMENT

(71) Applicant: Intuitive Surgical Operations, Inc., Sunnyvale, CA (US)

(72) Inventors: Nicola Diolaiti, Menlo Park, CA (US); Paul E. Lilagan, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 343 days.

This patent is subject to a terminal disclaimer.

(21) Appl. No.: 15/454,085

(22) Filed: Mar. 9, 2017

(65) Prior Publication Data

US 2017/0173788 A1 Jun. 22, 2017

Related U.S. Application Data

(63) Continuation of application No. 14/551,283, filed on Nov. 24, 2014, now Pat. No. 9,622,826, which is a
(Continued)

(51) Int. Cl.
*G06F 19/00* (2018.01)
*B25J 9/16* (2006.01)
(Continued)

(52) U.S. Cl.
CPC .............. *B25J 9/161* (2013.01); *A61B 34/25* (2016.02); *A61B 34/30* (2016.02); *A61B 34/37* (2016.02);
(Continued)

(58) Field of Classification Search
CPC ......... B25J 9/161; B25J 9/1633; A61B 34/74; A61B 34/37; A61B 34/25; A61B 34/77;
(Continued)

(56) References Cited

U.S. PATENT DOCUMENTS 3,628,535 A 12/1971 Ostrowsky et al.
3,818,284 A 6/1974 Deversterre et al.
(Continued)

FOREIGN PATENT DOCUMENTS

CN 101160104 A 4/2008
EP 514584 A2 11/1992
(Continued)

OTHER PUBLICATIONS

Azuma et al., "Recent Advances in Augmented Reality," IEEE Computer Graphics and Applications, Dec. 2001, 14 pages.
(Continued)

*Primary Examiner* — Ian Jen

(57) ABSTRACT

A medical robotic system includes an entry guide with articulated instruments extending out of its distal end. A controller is configured to command manipulation of one of the articulated instruments towards a state commanded by operator manipulation of an input device while commanding sensory feedback to the operator indicating a difference between the commanded state and a preferred pose of the articulated instrument, so that the sensory feedback serves to encourage the operator to return the articulated instrument back to its preferred pose.

20 Claims, 10 Drawing Sheets

Related U.S. Application Data continuation of application No. 12/704,669, filed on Feb. 12, 2010, now Pat. No. 8,918,211.

(51) Int. Cl.

| | | |
|---|---|---|
| *A61B 34/00* | (2016.01) | |
| *A61B 34/37* | (2016.01) | |
| *A61B 34/30* | (2016.01) | |
| *A61B 34/10* | (2016.01) | |
| *A61B 90/00* | (2016.01) | |
| *A61B 90/30* | (2016.01) | |

(52) U.S. Cl.
CPC .............. *A61B 34/74* (2016.02); *A61B 34/76* (2016.02); *A61B 34/77* (2016.02); *B25J 9/1633* (2013.01); *A61B 90/361* (2016.02); *A61B 2034/102* (2016.02); *A61B 2034/305* (2016.02); *A61B 2034/741* (2016.02); *A61B 2034/742* (2016.02); *A61B 2034/743* (2016.02); *A61B 2034/744* (2016.02); *A61B 2090/306* (2016.02); *Y10S 901/33* (2013.01); *Y10S 901/34* (2013.01)

(58) Field of Classification Search
CPC ... A61B 34/76; A61B 34/30; A61B 2034/743; A61B 2034/742; A61B 2034/741; A61B 2034/744; A61B 90/361; A61B 2090/306; A61B 2034/305; A61B 2034/102; Y10S 901/33; Y10S 901/34

See application file for complete search history.

(56) References Cited

U.S. PATENT DOCUMENTS

| | | |
|---|---|---|
| 3,905,215 A | 9/1975 | Wright |
| 3,923,166 A | 12/1975 | Fletcher et al. |
| 4,150,326 A | 4/1979 | Engelberger et al. |
| 4,349,837 A | 9/1982 | Hinds |
| 4,577,621 A | 3/1986 | Patel |
| 4,588,348 A | 5/1986 | Beni et al. |
| 4,644,237 A | 2/1987 | Frushour et al. |
| 4,672,963 A | 6/1987 | Barken |
| 4,722,056 A | 1/1988 | Roberts et al. |
| 4,759,074 A | 7/1988 | Iadipaolo et al. |
| 4,762,455 A | 8/1988 | Coughlan et al. |
| 4,762,456 A | 8/1988 | Nelson |
| 4,791,934 A | 12/1988 | Brunnett |
| 4,815,450 A | 3/1989 | Patel |
| 4,831,549 A | 5/1989 | Red et al. |
| 4,833,383 A | 5/1989 | Skarr et al. |
| 4,837,703 A | 6/1989 | Kakazu et al. |
| 4,837,734 A | 6/1989 | Ichikawa et al. |
| 4,839,838 A | 6/1989 | Labiche et al. |
| 4,853,874 A | 8/1989 | Iwamoto et al. |
| 4,858,149 A | 8/1989 | Quarendon |
| 4,860,215 A | 8/1989 | Seraji |
| 4,863,133 A | 9/1989 | Bonnell |
| 4,891,767 A | 1/1990 | Rzasa et al. |
| 4,942,539 A | 7/1990 | McGee et al. |
| 4,979,949 A | 12/1990 | Matsen, III |
| 4,984,157 A | 1/1991 | Cline et al. |
| 4,989,253 A | 1/1991 | Liang et al. |
| 5,046,022 A | 9/1991 | Conway et al. |
| 5,053,976 A | 10/1991 | Nose et al. |
| 5,079,699 A | 1/1992 | Tuy et al. |
| 5,086,401 A | 2/1992 | Glassman et al. |
| 5,098,426 A | 3/1992 | Sklar et al. |
| 5,099,846 A | 3/1992 | Hardy |
| 5,142,930 A | 9/1992 | Allen et al. |
| 5,170,347 A | 12/1992 | Tuy et al. |
| 5,174,276 A | 12/1992 | Crockard |
| 5,176,702 A | 1/1993 | Bales et al. |
| 5,182,641 A | 1/1993 | Diner et al. |
| 5,184,009 A | 2/1993 | Wright et al. |
| 5,184,601 A | 2/1993 | Putman |
| 5,187,796 A | 2/1993 | Wang et al. |
| 5,217,003 A | 6/1993 | Wilk |
| 5,230,338 A | 7/1993 | Allen et al. |
| 5,230,623 A | 7/1993 | Guthrie et al. |
| 5,235,510 A | 8/1993 | Yamada et al. |
| 5,239,246 A | 8/1993 | Kim |
| 5,251,127 A | 10/1993 | Raab |
| 5,251,611 A | 10/1993 | Zehel et al. |
| 5,257,203 A | 10/1993 | Riley et al. |
| 5,261,404 A | 11/1993 | Mick et al. |
| 5,266,875 A | 11/1993 | Slotine et al. |
| 5,279,309 A | 1/1994 | Taylor et al. |
| 5,299,288 A | 3/1994 | Glassman et al. |
| 5,313,306 A | 5/1994 | Kuban et al. |
| 5,321,353 A | 6/1994 | Furness |
| 5,337,733 A | 8/1994 | Bauerfeind et al. |
| 5,341,950 A | 8/1994 | Sinz |
| 5,343,385 A | 8/1994 | Joskowicz et al. |
| 5,368,015 A | 11/1994 | Wilk |
| 5,368,428 A | 11/1994 | Hussey et al. |
| 5,382,885 A | 1/1995 | Salcudean et al. |
| 5,397,323 A | 3/1995 | Taylor et al. |
| 5,402,801 A | 4/1995 | Taylor |
| 5,408,409 A | 4/1995 | Glassman et al. |
| 5,417,210 A | 5/1995 | Funda et al. |
| 5,430,643 A | 7/1995 | Seraji |
| 5,445,166 A | 8/1995 | Taylor |
| 5,454,827 A | 10/1995 | Aust et al. |
| 5,474,571 A | 12/1995 | Lang |
| 5,482,029 A | 1/1996 | Sekiguchi et al. |
| 5,493,595 A | 2/1996 | Schoolman |
| 5,503,320 A | 4/1996 | Webster et al. |
| 5,515,478 A | 5/1996 | Wang |
| 5,524,180 A | 6/1996 | Wang et al. |
| 5,528,955 A | 6/1996 | Hannaford et al. |
| 5,531,742 A | 7/1996 | Barken |
| 5,551,432 A | 9/1996 | Iezzi |
| 5,553,198 A | 9/1996 | Wang et al. |
| 5,572,999 A | 11/1996 | Funda et al. |
| 5,601,549 A | 2/1997 | Miyagi |
| 5,617,858 A | 4/1997 | Taverna et al. |
| 5,624,398 A | 4/1997 | Smith et al. |
| 5,631,973 A | 5/1997 | Green |
| 5,638,819 A | 6/1997 | Manwaring et al. |
| 5,657,429 A | 8/1997 | Wang et al. |
| 5,695,500 A | 12/1997 | Taylor et al. |
| 5,704,897 A | 1/1998 | Truppe |
| 5,715,729 A | 2/1998 | Toyama et al. |
| 5,737,500 A | 4/1998 | Seraji et al. |
| 5,748,767 A | 5/1998 | Raab |
| 5,749,362 A | 5/1998 | Funda et al. |
| 5,754,741 A | 5/1998 | Wang et al. |
| 5,755,725 A | 5/1998 | Druais |
| 5,759,151 A | 6/1998 | Sturges |
| 5,759,153 A | 6/1998 | Webler et al. |
| 5,762,458 A | 6/1998 | Wang et al. |
| 5,765,561 A | 6/1998 | Chen et al. |
| 5,784,542 A | 7/1998 | Ohm et al. |
| 5,788,688 A | 8/1998 | Bauer et al. |
| 5,791,231 A | 8/1998 | Cohn et al. |
| 5,792,135 A | 8/1998 | Madhani et al. |
| 5,797,849 A | 8/1998 | Vesely et al. |
| 5,797,900 A | 8/1998 | Madhani et al. |
| 5,807,377 A | 9/1998 | Madhani et al. |
| 5,808,665 A | 9/1998 | Green |
| 5,810,008 A | 9/1998 | Dekel et al. |
| 5,810,880 A | 9/1998 | Jensen et al. |
| 5,814,038 A | 9/1998 | Jensen et al. |
| 5,815,640 A | 9/1998 | Wang et al. |
| 5,817,022 A | 10/1998 | Vesely |
| 5,820,545 A | 10/1998 | Arbter et al. |
| 5,820,623 A | 10/1998 | Ng |
| 5,831,408 A | 11/1998 | Jacobus et al. |
| 5,835,693 A | 11/1998 | Lynch et al. |
| 5,836,880 A | 11/1998 | Pratt |
| 5,841,950 A | 11/1998 | Wang et al. |
| 5,842,473 A | 12/1998 | Fenster et al. |

(56) References Cited

U.S. PATENT DOCUMENTS

| | | |
|---|---|---|
| 5,842,993 A | 12/1998 | Eichelberger et al. |
| 5,853,367 A | 12/1998 | Chalek et al. |
| 5,855,553 A | 1/1999 | Tajima et al. |
| 5,855,583 A | 1/1999 | Wang et al. |
| 5,859,934 A | 1/1999 | Green |
| 5,876,325 A | 3/1999 | Mizuno et al. |
| 5,877,819 A | 3/1999 | Branson |
| 5,878,193 A | 3/1999 | Wang et al. |
| 5,887,121 A | 3/1999 | Funda et al. |
| 5,907,664 A | 5/1999 | Wang et al. |
| 5,911,036 A | 6/1999 | Wright et al. |
| 5,931,832 A | 8/1999 | Jensen |
| 5,938,678 A | 8/1999 | Zirps et al. |
| 5,950,629 A | 9/1999 | Taylor et al. |
| 5,964,707 A | 10/1999 | Fenster et al. |
| 5,971,976 A | 10/1999 | Wang et al. |
| 5,980,460 A | 11/1999 | Oestensen et al. |
| 5,980,461 A | 11/1999 | Rajan |
| 5,987,591 A | 11/1999 | Jyumonji |
| 5,993,390 A | 11/1999 | Savord et al. |
| 5,993,391 A | 11/1999 | Kamiyama |
| 6,019,724 A | 2/2000 | Gronningsaeter et al. |
| 6,036,637 A | 3/2000 | Kudo |
| 6,059,718 A | 5/2000 | Taniguchi et al. |
| 6,063,095 A | 5/2000 | Wang et al. |
| 6,072,466 A | 6/2000 | Shah et al. |
| 6,083,170 A | 7/2000 | Ben-Haim |
| 6,084,371 A | 7/2000 | Kress et al. |
| 6,096,025 A | 8/2000 | Borders |
| 6,115,053 A | 9/2000 | Perlin |
| 6,120,433 A | 9/2000 | Mizuno |
| 6,129,670 A | 10/2000 | Burdette et al. |
| 6,184,868 B1 | 2/2001 | Shahoian et al. |
| 6,196,081 B1 | 3/2001 | Yau |
| 6,201,984 B1 | 3/2001 | Funda et al. |
| 6,204,620 B1 | 3/2001 | McGee et al. |
| 6,224,542 B1 | 5/2001 | Chang et al. |
| 6,226,566 B1 | 5/2001 | Funda et al. |
| 6,241,725 B1 | 6/2001 | Cosman |
| 6,243,624 B1 | 6/2001 | Wu et al. |
| 6,246,200 B1 | 6/2001 | Blumenkranz et al. |
| 6,256,529 B1 | 7/2001 | Holupka et al. |
| 6,270,453 B1 | 8/2001 | Sakai |
| 6,292,712 B1 | 9/2001 | Bullen |
| 6,307,285 B1 | 10/2001 | Delson et al. |
| 6,312,435 B1 | 11/2001 | Wallace et al. |
| 6,325,808 B1 | 12/2001 | Bernard et al. |
| 6,330,837 B1 | 12/2001 | Charles et al. |
| 6,331,181 B1 | 12/2001 | Tierney et al. |
| 6,342,889 B1 | 1/2002 | Callahan |
| 6,358,749 B1 | 3/2002 | Orthman |
| 6,371,909 B1 | 4/2002 | Hoeg et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,402,737 B1 | 6/2002 | Tajima et al. |
| 6,424,885 B1 | 7/2002 | Niemeyer et al. |
| 6,425,865 B1 | 7/2002 | Salcudean et al. |
| 6,434,416 B1 | 8/2002 | Mizoguchi et al. |
| 6,436,107 B1 | 8/2002 | Wang et al. |
| 6,442,417 B1 | 8/2002 | Shahidi et al. |
| 6,456,901 B1 | 9/2002 | Xi et al. |
| 6,459,926 B1 | 10/2002 | Nowlin et al. |
| 6,468,265 B1 | 10/2002 | Evans et al. |
| 6,493,608 B1 | 12/2002 | Niemeyer |
| 6,522,906 B1 | 2/2003 | Salisbury, Jr. et al. |
| 6,522,908 B1 | 2/2003 | Miyashita et al. |
| 6,547,782 B1 | 4/2003 | Taylor |
| 6,550,757 B2 | 4/2003 | Sesek |
| 6,569,084 B1 | 5/2003 | Mizuno et al. |
| 6,574,355 B2 | 6/2003 | Green |
| 6,594,522 B1 | 7/2003 | Korenaga |
| 6,594,552 B1 | 7/2003 | Nowlin et al. |
| 6,599,247 B1 | 7/2003 | Stetten |
| 6,602,185 B1 | 8/2003 | Uchikubo |
| 6,620,173 B2 | 9/2003 | Gerbi et al. |
| 6,642,836 B1 | 11/2003 | Wang et al. |
| 6,643,563 B2 | 11/2003 | Hosek et al. |
| 6,645,196 B1 | 11/2003 | Nixon et al. |
| 6,648,816 B2 | 11/2003 | Irion et al. |
| 6,654,031 B1 | 11/2003 | Ito et al. |
| 6,659,939 B2 | 12/2003 | Moll et al. |
| 6,665,554 B1 | 12/2003 | Charles et al. |
| 6,671,581 B2 | 12/2003 | Niemeyer et al. |
| 6,676,669 B2 | 1/2004 | Charles et al. |
| 6,699,177 B1 | 3/2004 | Wang et al. |
| 6,702,736 B2 | 3/2004 | Chen et al. |
| 6,714,839 B2 | 3/2004 | Salisbury et al. |
| 6,765,569 B2 | 7/2004 | Neumann et al. |
| 6,770,081 B1 | 8/2004 | Cooper et al. |
| 6,786,896 B1 | 9/2004 | Madhani et al. |
| 6,799,065 B1 | 9/2004 | Niemeyer |
| 6,817,973 B2 | 11/2004 | Merril et al. |
| 6,827,712 B2 | 12/2004 | Tovey et al. |
| 6,837,883 B2 | 1/2005 | Moll et al. |
| 6,847,922 B1 | 1/2005 | Wampler, II |
| 6,852,107 B2 | 2/2005 | Wang et al. |
| 6,876,891 B1 | 4/2005 | Schuler et al. |
| 6,905,460 B2 | 6/2005 | Wang et al. |
| 6,926,709 B2 | 8/2005 | Bieger et al. |
| 6,960,162 B2 | 11/2005 | Saadat et al. |
| 6,984,203 B2 | 1/2006 | Tartaglia et al. |
| 6,991,627 B2 | 1/2006 | Madhani et al. |
| 7,041,053 B2 | 5/2006 | Miyake |
| 7,107,090 B2 | 9/2006 | Salisbury et al. |
| 7,107,124 B2 | 9/2006 | Green |
| 7,144,367 B2 | 12/2006 | Chen et al. |
| 7,155,315 B2 | 12/2006 | Niemeyer et al. |
| 7,155,316 B2 | 12/2006 | Sutherland et al. |
| 7,181,315 B2 | 2/2007 | Watanabe et al. |
| 7,194,118 B1 | 3/2007 | Harris et al. |
| 7,302,288 B1 | 11/2007 | Schellenberg |
| 7,413,565 B2 | 8/2008 | Wang et al. |
| 7,491,198 B2 | 2/2009 | Kockro |
| 7,493,153 B2 | 2/2009 | Ahmed et al. |
| 7,574,250 B2 | 8/2009 | Niemeyer |
| 7,725,214 B2 * | 5/2010 | Diolaiti .............. A61B 1/00087 700/247 |
| 7,806,891 B2 | 10/2010 | Nowlin et al. |
| 7,819,859 B2 | 10/2010 | Prisco et al. |
| 7,963,913 B2 | 6/2011 | Devengenzo et al. |
| 7,979,157 B2 | 7/2011 | Anvari |
| 7,996,110 B2 | 8/2011 | Lipow et al. |
| 7,998,058 B2 | 8/2011 | Kura et al. |
| 8,004,229 B2 | 8/2011 | Nowlin et al. |
| 8,005,571 B2 | 8/2011 | Sutherland et al. |
| 8,062,288 B2 | 11/2011 | Cooper et al. |
| 8,108,072 B2 | 1/2012 | Zhao et al. |
| 8,120,301 B2 | 2/2012 | Goldberg et al. |
| 8,130,907 B2 | 3/2012 | Maurer, Jr. et al. |
| 8,155,479 B2 | 4/2012 | Hoffman et al. |
| 8,170,716 B2 | 5/2012 | Coste-Maniere et al. |
| 8,175,861 B2 | 5/2012 | Huang et al. |
| 8,221,304 B2 | 7/2012 | Shioda et al. |
| 8,256,319 B2 | 9/2012 | Cooper et al. |
| 8,306,656 B1 | 11/2012 | Schaible et al. |
| 8,315,720 B2 | 11/2012 | Mohr et al. |
| 8,335,590 B2 * | 12/2012 | Costa .................. B25J 9/1697 700/245 |
| 8,398,541 B2 * | 3/2013 | DiMaio .................. A61B 34/10 600/111 |
| 8,541,970 B2 | 9/2013 | Nowlin et al. |
| 8,554,368 B2 * | 10/2013 | Fielding ................ B25J 9/1689 700/247 |
| 8,620,473 B2 * | 12/2013 | Diolaiti .................. A61B 90/37 700/245 |
| 8,624,537 B2 | 1/2014 | Nowlin et al. |
| 8,749,189 B2 | 6/2014 | Nowlin et al. |
| 8,749,190 B2 | 6/2014 | Nowlin et al. |
| 8,786,241 B2 | 7/2014 | Nowlin et al. |
| 8,816,628 B2 | 8/2014 | Nowlin et al. |
| 8,823,308 B2 | 9/2014 | Nowlin et al. |
| 8,864,652 B2 * | 10/2014 | Diolaiti .............. A61B 1/00009 600/102 |

(56) References Cited

U.S. PATENT DOCUMENTS

| | | | |
|---|---|---|---|
| 8,903,546 B2 * | 12/2014 | Diolaiti | A61B 34/30 |
| | | | 700/245 |
| 8,918,211 B2 * | 12/2014 | Diolaiti | B25J 9/161 |
| | | | 700/257 |
| 8,944,070 B2 * | 2/2015 | Guthart | A61B 8/12 |
| | | | 128/898 |
| 9,084,623 B2 * | 7/2015 | Gomez | B25J 9/1656 |
| 9,089,256 B2 * | 7/2015 | Tognaccini | A61B 1/00183 |
| 9,101,397 B2 | 8/2015 | Guthart et al. | |
| 9,138,129 B2 * | 9/2015 | Diolaiti | A61B 1/00163 |
| 9,232,984 B2 | 1/2016 | Guthart et al. | |
| 9,333,042 B2 | 5/2016 | Diolaiti et al. | |
| 9,345,387 B2 | 5/2016 | Larkin | |
| 9,469,034 B2 | 10/2016 | Diolaiti et al. | |
| 9,492,927 B2 * | 11/2016 | Diolaiti | B25J 9/1689 |
| 9,516,996 B2 | 12/2016 | Diolaiti et al. | |
| 9,565,990 B2 | 2/2017 | Lee et al. | |
| 9,622,826 B2 | 4/2017 | Diolaiti et al. | |
| 9,629,520 B2 | 4/2017 | Diolaiti | |
| 9,717,563 B2 | 8/2017 | Tognaccini et al. | |
| 9,718,190 B2 | 8/2017 | Larkin et al. | |
| 9,949,798 B2 | 4/2018 | Weir et al. | |
| 2001/0035871 A1 | 11/2001 | Bieger et al. | |
| 2002/0044104 A1 | 4/2002 | Friedrich et al. | |
| 2002/0045888 A1 | 4/2002 | Ramans et al. | |
| 2002/0089544 A1 | 7/2002 | Jahn et al. | |
| 2002/0120188 A1 | 8/2002 | Brock et al. | |
| 2002/0156345 A1 | 10/2002 | Eppler et al. | |
| 2002/0193800 A1 | 12/2002 | Kienzle, III | |
| 2003/0023347 A1 | 1/2003 | Konno et al. | |
| 2003/0032878 A1 | 2/2003 | Shahidi | |
| 2003/0055410 A1 | 3/2003 | Evans et al. | |
| 2003/0060927 A1 | 3/2003 | Gerbi et al. | |
| 2003/0109780 A1 | 6/2003 | Coste-Maniere et al. | |
| 2003/0114730 A1 | 6/2003 | Hale et al. | |
| 2003/0144649 A1 | 7/2003 | Ghodoussi et al. | |
| 2003/0167103 A1 | 9/2003 | Tang et al. | |
| 2003/0225479 A1 | 12/2003 | Waled | |
| 2004/0024311 A1 | 2/2004 | Quaid et al. | |
| 2004/0034283 A1 | 2/2004 | Quaid, III | |
| 2004/0039485 A1 | 2/2004 | Niemeyer et al. | |
| 2004/0044295 A1 | 3/2004 | Reinert et al. | |
| 2004/0046711 A1 | 3/2004 | Triebfuerst | |
| 2004/0046916 A1 | 3/2004 | Lyu et al. | |
| 2004/0049205 A1 | 3/2004 | Lee et al. | |
| 2004/0077940 A1 | 4/2004 | Kienzle et al. | |
| 2004/0106916 A1 | 6/2004 | Quaid et al. | |
| 2004/0176751 A1 | 9/2004 | Weitzner et al. | |
| 2004/0189675 A1 | 9/2004 | Pretlove et al. | |
| 2004/0225183 A1 | 11/2004 | Michlitsch et al. | |
| 2004/0238732 A1 | 12/2004 | State et al. | |
| 2004/0243147 A1 | 12/2004 | Lipow | |
| 2004/0249508 A1 | 12/2004 | Suita et al. | |
| 2004/0254454 A1 | 12/2004 | Kockro | |
| 2004/0254679 A1 | 12/2004 | Nagasaka | |
| 2005/0022158 A1 | 1/2005 | Launay et al. | |
| 2005/0054895 A1 | 3/2005 | Hoeg et al. | |
| 2005/0059960 A1 | 3/2005 | Simaan et al. | |
| 2005/0096502 A1 | 5/2005 | Khalili | |
| 2005/0096892 A1 | 5/2005 | Watanabe et al. | |
| 2005/0107680 A1 | 5/2005 | Kopf et al. | |
| 2005/0113640 A1 | 5/2005 | Saadat | |
| 2005/0166413 A1 | 8/2005 | Crampton et al. | |
| 2005/0203380 A1 | 9/2005 | Sauer et al. | |
| 2005/0228365 A1 | 10/2005 | Wang | |
| 2005/0251113 A1 | 11/2005 | Kienzle, III | |
| 2005/0267359 A1 | 12/2005 | Hussaini et al. | |
| 2006/0058988 A1 | 3/2006 | Defranoux et al. | |
| 2006/0142657 A1 | 6/2006 | Quaid et al. | |
| 2006/0149129 A1 | 7/2006 | Watts et al. | |
| 2006/0161045 A1 | 7/2006 | Merril et al. | |
| 2006/0161138 A1 | 7/2006 | Orban, III | |
| 2006/0178559 A1 | 8/2006 | Kumar et al. | |
| 2006/0258938 A1 | 11/2006 | Hoffman et al. | |
| 2006/0261770 A1 | 11/2006 | Kishi et al. | |
| 2007/0013336 A1 | 1/2007 | Nowlin et al. | |
| 2007/0016174 A1 | 1/2007 | Millman et al. | |
| 2007/0021738 A1 | 1/2007 | Hasser et al. | |
| 2007/0038080 A1 | 2/2007 | Salisbury, Jr. et al. | |
| 2007/0060879 A1 | 3/2007 | Weitzner et al. | |
| 2007/0071310 A1 | 3/2007 | Kobayashi et al. | |
| 2007/0081714 A1 | 4/2007 | Wallack et al. | |
| 2007/0106307 A1 | 5/2007 | Bodduluri et al. | |
| 2007/0135803 A1 | 6/2007 | Belson | |
| 2007/0138992 A1 | 6/2007 | Prisco et al. | |
| 2007/0142825 A1 | 6/2007 | Prisco et al. | |
| 2007/0142968 A1 | 6/2007 | Prisco et al. | |
| 2007/0144298 A1 | 6/2007 | Miller | |
| 2007/0156285 A1 | 7/2007 | Sillman et al. | |
| 2007/0177009 A1 | 8/2007 | Bayer et al. | |
| 2007/0197896 A1 | 8/2007 | Moll et al. | |
| 2007/0229015 A1 | 10/2007 | Yoshida et al. | |
| 2007/0255454 A1 | 11/2007 | Dariush | |
| 2007/0265491 A1 | 11/2007 | Krag et al. | |
| 2007/0270650 A1 | 11/2007 | Eno et al. | |
| 2007/0270685 A1 | 11/2007 | Kang et al. | |
| 2007/0283970 A1 | 12/2007 | Mohr et al. | |
| 2007/0287884 A1 | 12/2007 | Schena | |
| 2007/0287992 A1 | 12/2007 | Diolaiti et al. | |
| 2007/0296366 A1 | 12/2007 | Quaid et al. | |
| 2008/0004603 A1 | 1/2008 | Larkin et al. | |
| 2008/0033240 A1 | 2/2008 | Hoffman et al. | |
| 2008/0065099 A1 | 3/2008 | Cooper et al. | |
| 2008/0065105 A1 | 3/2008 | Larkin et al. | |
| 2008/0071291 A1 | 3/2008 | Duval et al. | |
| 2008/0081992 A1 | 4/2008 | Kagermeier | |
| 2008/0118115 A1 | 5/2008 | Williamson | |
| 2008/0140087 A1 | 6/2008 | Barbagli | |
| 2008/0161830 A1 | 7/2008 | Sutherland et al. | |
| 2008/0188986 A1 | 8/2008 | Hoppe | |
| 2008/0243142 A1 | 10/2008 | Gildenberg | |
| 2008/0247506 A1 | 10/2008 | Maschke | |
| 2008/0287963 A1 | 11/2008 | Rogers et al. | |
| 2009/0005640 A1 | 1/2009 | Fehre et al. | |
| 2009/0012531 A1 | 1/2009 | Quaid et al. | |
| 2009/0024142 A1 | 1/2009 | Ruiz | |
| 2009/0088634 A1 | 4/2009 | Zhao et al. | |
| 2009/0105750 A1 | 4/2009 | Price et al. | |
| 2009/0192523 A1 | 7/2009 | Larkin et al. | |
| 2009/0192524 A1 | 7/2009 | Itkowitz et al. | |
| 2009/0228145 A1 | 9/2009 | Hodgson et al. | |
| 2009/0248036 A1 | 10/2009 | Hoffman et al. | |
| 2009/0259105 A1 | 10/2009 | Miyano et al. | |
| 2009/0326322 A1 | 12/2009 | Diolaiti | |
| 2009/0326552 A1 | 12/2009 | Diolaiti | |
| 2009/0326553 A1 | 12/2009 | Mustufa et al. | |
| 2009/0326711 A1 | 12/2009 | Chang et al. | |
| 2010/0004505 A1 | 1/2010 | Umemoto et al. | |
| 2010/0036198 A1 | 2/2010 | Tacchino et al. | |
| 2010/0106356 A1 | 4/2010 | Trepagnier et al. | |
| 2010/0169815 A1 | 7/2010 | Zhao et al. | |
| 2010/0198232 A1 | 8/2010 | Diolaiti | |
| 2010/0228264 A1 | 9/2010 | Robinson et al. | |
| 2010/0249657 A1 | 9/2010 | Nycz et al. | |
| 2010/0317965 A1 | 12/2010 | Itkowitz et al. | |
| 2010/0328363 A1 | 12/2010 | Nakanishi | |
| 2010/0331855 A1 | 12/2010 | Zhao et al. | |
| 2010/0331856 A1 | 12/2010 | Carlson et al. | |
| 2011/0071675 A1 | 3/2011 | Wells et al. | |
| 2011/0196199 A1 | 8/2011 | Donhowe et al. | |
| 2011/0290856 A1 | 12/2011 | Shelton, IV et al. | |
| 2011/0313573 A1 | 12/2011 | Schreiber et al. | |
| 2012/0059391 A1 | 3/2012 | Diolaiti et al. | |
| 2012/0132450 A1 | 5/2012 | Timm et al. | |
| 2012/0154564 A1 | 6/2012 | Hoffman et al. | |
| 2013/0178868 A1 | 7/2013 | Roh | |
| 2013/0231680 A1 | 9/2013 | Diolaiti et al. | |
| 2013/0245375 A1 | 9/2013 | Dimaio et al. | |
| 2013/0289767 A1 | 10/2013 | Lim et al. | |
| 2014/0052150 A1 | 2/2014 | Taylor et al. | |
| 2014/0055489 A1 | 2/2014 | Itkowitz et al. | |
| 2014/0135792 A1 | 5/2014 | Larkin et al. | |
| 2014/0232824 A1 | 8/2014 | Dimaio et al. | |
| 2015/0032126 A1 | 1/2015 | Nowlin et al. | |

(56) References Cited

U.S. PATENT DOCUMENTS

| | | |
|---|---|---|
| 2015/0051733 A1 | 2/2015 | Nowlin et al. |
| 2015/0065793 A1 | 3/2015 | Diolaiti et al. |
| 2015/0150639 A1 | 6/2015 | Diolaiti et al. |
| 2015/0182287 A1 | 7/2015 | Guthart et al. |
| 2015/0297300 A1 | 10/2015 | Gomez et al. |
| 2015/0366625 A1 | 12/2015 | Tognaccini et al. |
| 2016/0045272 A1 | 2/2016 | Diolaiti |
| 2016/0235486 A1 | 8/2016 | Larkin |
| 2016/0242860 A1 | 8/2016 | Diolaiti et al. |
| 2016/0374767 A1 | 12/2016 | Diolaiti et al. |
| 2017/0035521 A1 | 2/2017 | Diolaiti et al. |
| 2017/0173788 A1 | 6/2017 | Diolaiti et al. |
| 2017/0209232 A1 | 7/2017 | Larkin et al. |
| 2017/0210012 A1 | 7/2017 | Larkin et al. |

FOREIGN PATENT DOCUMENTS

| | | |
|---|---|---|
| EP | 0646358 A1 | 4/1995 |
| EP | 812662 A1 | 12/1997 |
| EP | 1125557 A2 | 8/2001 |
| EP | 0732082 B1 | 9/2002 |
| EP | 1310844 A1 | 5/2003 |
| EP | 1424173 A2 | 6/2004 |
| JP | H01280449 A | 11/1989 |
| JP | H04231034 A | 8/1992 |
| JP | H07184923 A | 7/1995 |
| JP | H07265321 A | 10/1995 |
| JP | H0889506 A | 4/1996 |
| JP | H08107875 A | 4/1996 |
| JP | H08132372 A | 5/1996 |
| JP | H08154321 A | 6/1996 |
| JP | H08215211 A | 8/1996 |
| JP | H08275958 A | 10/1996 |
| JP | H08299363 A | 11/1996 |
| JP | H09141580 A | 6/1997 |
| JP | H10146341 A | 6/1998 |
| JP | H11309 A | 1/1999 |
| JP | 2000500679 A | 1/2000 |
| JP | 2000300579 A | 10/2000 |
| JP | 2001000448 A | 1/2001 |
| JP | 2001061850 A | 3/2001 |
| JP | 2001104333 A | 4/2001 |
| JP | 2001202531 A | 7/2001 |
| JP | 2001287183 A | 10/2001 |
| JP | 2002103258 A | 4/2002 |
| JP | 2002287613 A | 10/2002 |
| JP | 2003053684 A | 2/2003 |
| JP | 2003300444 A | 10/2003 |
| JP | 2003339725 A | 12/2003 |
| JP | 2004105638 A | 4/2004 |
| JP | 2004223128 A | 8/2004 |
| JP | 2005110878 A | 4/2005 |
| JP | 2005135278 A | 5/2005 |
| JP | 2005303327 A | 10/2005 |
| JP | 2005334650 A | 12/2005 |
| JP | 2007029232 A | 2/2007 |
| JP | 2007090481 A | 4/2007 |
| JP | 2007508913 A | 4/2007 |
| JP | 2007531553 A | 11/2007 |
| JP | 2009006410 A | 1/2009 |
| JP | 2009012106 A | 1/2009 |
| JP | 2009039814 A | 2/2009 |
| JP | 2009525097 A | 7/2009 |
| JP | 2009537229 A | 10/2009 |
| KR | 20090111308 A | 10/2009 |
| WO | WO-9501757 A1 | 1/1995 |
| WO | WO-9507055 A1 | 3/1995 |
| WO | WO-9729690 A1 | 8/1997 |
| WO | WO-9743942 A1 | 11/1997 |
| WO | WO-9743943 A1 | 11/1997 |
| WO | WO-03061482 A1 | 7/2003 |
| WO | WO-2004014244 A2 | 2/2004 |
| WO | WO-2005037120 A1 | 4/2005 |
| WO | WO-2005039391 A2 | 5/2005 |
| WO | WO-2005043319 A2 | 5/2005 |
| WO | WO-2006079108 A1 | 7/2006 |
| WO | WO-2006091494 A1 | 8/2006 |
| WO | WO-2007005555 A2 | 1/2007 |
| WO | WO-2007030173 A1 | 3/2007 |
| WO | WO-2007047782 A2 | 4/2007 |
| WO | WO-2007088206 A2 | 8/2007 |
| WO | WO-2007088208 A2 | 8/2007 |
| WO | WO-2007136768 A2 | 11/2007 |
| WO | WO-2007146987 A2 | 12/2007 |
| WO | WO-2008002830 A2 | 1/2008 |
| WO | WO-2008094766 A2 | 8/2008 |
| WO | WO-2008103383 A1 | 8/2008 |
| WO | WO-2009034477 A2 | 3/2009 |
| WO | WO-2009037576 A2 | 3/2009 |
| WO | WO-2009044287 A2 | 4/2009 |
| WO | WO-2009158164 A1 | 12/2009 |
| WO | WO-2010039394 A1 | 4/2010 |

OTHER PUBLICATIONS

Lievin et al., "Stereoscopic Augmented Reality System for Computer Assisted Surgery," CARS 2001, Jun. 27-30, 2001, pp. 34-47.
3D Slicer, http://slicer.org/welcome.html, downloaded Oct. 25, 2006, p. 1; and Introduction, http:/slicer.org/intro/index.html, downloaded Oct. 25, 2006, pp. 1-4.
Abolmaesumi, Purang et al., "A User Interface for Robot-Assisted Diagnostic Ultrasound," IEEE Robotics and Automation Conference, 2001, pp. 1549-1554, vol. 2, IEEE.
Abolmaesumi, Purang et al., "Image Guided Control of a Robot for Medical Ultrasound," IEEE Transactions on Robotics and Automation, 2002, pp. 11-23, vol. 18—Issue 1, IEEE.
Adams, Ludwig et al., "Computer-Assisted Surgery," IEEE Computer Graphics & Applications, May 1990, pp. 43-52, vol. 10—Issue 3, IEEE Computer Society Press.
Ahlering, Thomas. E. et al., "Robotic radical prostatectomy: a technique to reduce pT2 positive margins," Urology, 2004, pp. 1224-1228, vol. 64 Issue 6, Elsevier Inc.
Alexander, Arthur D. III, "Impacts of Telemation on Modern Society," Symposium on Theory and Practice of Robots and Manipulators, Centre for Mechanical Sciences 1st Cism IFToMM Symposium, Sep. 5-8, 1974, pp. 121-136, vol. 2, Springer-Verlag.
Arai, Tetsuo et al., "Bilateral control for manipulators with different configurations," IECON Inn Conference on Industrial Electronics Control and Instrumentation, Oct. 22-26 1984, pp. 40-45, vol. 1.
Arun, K.S. et al., "Least-Squares Fitting of Two 3-D Point Sets," IEEE Transactions on Pattern Analysis and Machine Intelligence (PAMI), vol. 9, No. 5, pp. 698-700, Sep. 1987.
Askew, Scott R. et al., "Ground control testbed for space station freedom robot manipulators," IEEE Virtual Reality Annual International Symposium, 1993, pp. 69-75, IEEE.
Azuma, Ronald T., "A Survey of Augmented Reality," Teleoperators and Virtual Environments, 1997, pp. 355-385, vol. 6—No. 4.
Bajura, Michael et al., "Merging Virtual Objects with the Real World: Seeing Ultrasound Imagery within the Patient," Computer Graphics, Jul. 26, 1992, pp. 203-210, vol. 26, Issue 2, ACM Press.
Banovac, Filip et al., "Liver Tumor Biopsy in a Respiring Phantom with the Assistance of a Novel Electromagnetic Navigation Device," 2002, pp. 200-207, Springer-Verlag.
Bartels, Richard H. et al., "An Introduction to Splines for use in Computer Graphics and Geometric Modeling," 1987, 6 Pages total , Morgan kaufmann publishers, INC.
Bartels, Richard H. et al., "Solution of the Matrix Equation AX+XB+ 32 C," Communications of the ACM, 1972, pp. 820-826, vol. 15—Issue 9, ACM Press.
Baumann, Roger, "Haptic Interface for Virtual Reality Based Laparoscopic Surgery Training Environment," These No. 1734 Ecole Pholytechnique Federale de Lausanne, 1997, 104 Total Pages.
Bejczy, Antal K. et al., "Controlling Remote Manipulators through Kinesthetic Coupling," Computers in Mechanical Engineering, 1983, pp. 48-60, vol. 1—Issue 1.
Ben Gayed, M. et al., "An Advanced Control Micromanipulator for Surgical Applications," Systems Science, 1987, pp. 123-134, vol. 13.

(56) References Cited

OTHER PUBLICATIONS

Berkelman, Peter J. et al., "A Compact Compliant Laparoscopic Endoscope Manipulator," IEEE International Conference on Robotics and Automation, 2002, pp. 1870-1875, vol. 2, IEEE.
Berkelman, Peter J. et al., "A miniature Instrument Tip Force Sensor for Robot/Human Cooperative Micro surgical Manipulation with Enhanced Force Feedback," Proceedings of the Third International Conference on Medical Image Computing and Computer-Assisted Intervention, Springer-Verlag, 2000, pp. 897-906, vol. 1935.
Berkelman, Peter J. et al., "A miniature microsurgical instrument tip force sensor for enhanced force feedback during robot-assisted manipulation," IEEE Transactions on Robotics and Automation, 2000, pp. 917-922, vol. 19—Issue 5, IEEE.
Berkelman, Peter J. et al., "Performance Evaluation of a Cooperative Manipulation Microsurgical Assistant Robot Applied to Stapedotomy," Medical Image Computing and Computer-Assisted Interventions, Lecture Notes in Computer Science, 2001, pp. 1426-1429, vol. 2208.
Besl, Paul J. et al., "A Method for Registration of 3-D Shapes," IEEE Transactions on Pattern Analysis and Machine Intelligence (PAMI), vol. 14, Issue 2, pp. 239-256, Feb. 1992.
Bettini, A. et al., "Vision Assisted Control for Manipulation Using Virtual Fixtures: Experiments at Macro and Micro Scales," IEEE Conference on Robots and Automation (ICRA '02), May 11-15, 2002, pp. 3354-3361, vol. 4, IEEE.
Bettini, A. et al., "Vision Assisted Control for Manipulation Using Virtual Fixtures," IEEE/RSJ International Conference on Intelligent Robots and Systems (IROS), Oct. 29-Nov. 3, 2001, pp. 1171-1176, vol. 2.
Bettini, Alessandro et al., "Vision Assisted Control for Manipulation Using Virtual Fixtures," IEEE Transactions on Robotics, 2004, pp. 953-966, vol. 20—Issue 6, IEEE.
Birkett, Desmond H., "Three-Dimensional Video Imaging Systems," Chapter 1 in Primer of Robotic & Telerobotic Surgery, Eds. Garth H. Ballantyne et al., Pub. by Lippincott Williams & Wilkins, Philadelphia, 2004, pp. 7-11. Sep. 5, 2019
Boctor, Emad et al., "A Novel Closed Form Solution for Ultrasound Calibration," IEEE International Symposium on Biomedical Imaging (ISBI), Arlington, VA, vol. 1, pp. 527-530, Apr. 15-18, 2004.
Boctor, Emad, M. et al., "A dual-armed robotic system for intraoperative ultrasound guided hepatic ablative therapy: a prospective study," Proc of IEEE 2004 International Conference on Robotics & Automation, 2004, pp. 2517-2522, vol. 3, IEEE.
Boctor, Emad, M. et al., "A Rapid calibration method for registration and 3D tracking of ultrasound images using spatial localizer," Ultrasonic Imaging and Signal Processing, 2003, pp. 521-532, vol. 5035, SPIE.
Boctor, Emad, M. et al., "CISUS: An integrated 3D ultrasound system for IGT using a modular tracking API," Proceedings of the SPIE, 2004, pp. 247-256, vol. 5367, SPIE.
Boctor, Emad, M. et al., "Development of a Robotically-Assisted 3-D Ultrasound System for Radiofrequency Ablation of Liver Tumors," 6th World Congress of the Hepato-Pancreato-Biliary Association, Abstract No. 167, 2004, pp. 46, vol. 6—Supplement 1, Taylor & Francis Health Science.
Boctor, Emad, M. et al., "PC Based system for calibration, Reconstruction Processing and Visualization of 3D Ultrasound Data Based on a Magnetic-Field Position and Orientation Sensing System," Proceedings of the International Conference on Computational Science—Part II, Lecture Notes in Computer Science, 2001, pp. 13-22, vol. 2074, Springer.
Boctor, Emad, M. et al., "Robot-assisted 3D strain imaging for monitoring thermal ablation of liver," Annual congress of the Society of American Gastrointestinal Endoscopic Surgeons (SAGES), Emerging Technology Lunch Poster TP004, 2005, pp. 240-241.
Boctor, Emad, M. et al., "Robotic Strain Imaging for Monitoring Thermal Ablation of Liver," Medical Image Computing and Computer-Assisted Intervention MICCAI, 2004, pp. 81-88, vol. 2, Springer-Verlag.
Boctor, Emad, M. et al., "Robotically assisted intraoperative ultrasound with application to ablative therapy of liver cancer," Medical Imaging:Visualization, Image Guided Procedures, and Display, 2003, pp. 281-291, vol. 5029, SPIE.
Boctor, Emad, M. et al., "Tracked 3D ultrasound in radio-frequency liver ablation," in Medical Imaging 2003:Ultrasonic Imaging and Signal Processing, 2003, pp. 174-182, vol. 5035, SPIE.
Borovoi, A.V., "Stability of a manipulator with force feedback," Izv. AN SSSR Mekhanika Tverdogo Teal, 1990, pp. 37-45, vol. 25—Issue 1, Allerton Press, Inc.
Boudet,Sylvie et al., "An Integrated Robotics and Medical Control Device to Quantify Atheromatous Plaques: Experiments on the Arteries of a Patient," Proc of IEE/RSH International Conference on Intelligent Robots and Systems, 1997, pp. 1533-1538, vol. 3.
Brown, Myron M. et al., "Advances in Computational Stereo," IEEE Transactions on Pattern Analysis and Machine Intelligence (PAMI), 2003, pp. 993-1008, vol. 25 Issue, IEEE.
Burdea, Grigore et al., "Dextrous Telerobotics with Force Feedback—an overview. Part 2: Control and Implementation," Robotica, 1991, pp. 291-298, vol. 9.
Burschka, Darius et al., "Scale-Invariant Registration of Monocular Endoscopic Images to CT-Scans for Sinus Surgery," Med Image Anal, 2004, pp. 413-421, vol. 2, Springer-Verlag.
Burschka, Darius et al., "Scale-invariant Registration of Monocular Stereo Images to 3D Surface Models," IEEE Int. Conf. on Robots and Systems, 2004, pp. 2581-2586, vol. 3, IEEE.
Burschka, Darius et al., "Navigating Inner Space: 3-D Assistance for Minimally Invasive Surgery," Robotics and Autonomous Systems, 2005, pp. 5-26, vol. 52—Issue 1, Elsevier.
Burschka, Darius et al., "Principle and Practice of Real-Time Visual Tracking for Navigation and Mapping," IEEE Workshop on Robotic Sensing: Robotics in the Automotive Industry, 2004, pp. 1-8, IEEE.
Bzostek, Andrew, "Computer-Integrated needle therapy systems: Implementation and Analysis," Computer Science, 2005, 379 pages.
Bzostek, Andrew et al., "A Testbed System for Robotically Assisted Percutaneous Pattern Therapy," Medical Image Computing and Computer-Assisted Surgery, Lecture Notes in Computer Science, 1999, pp. 1098-1107, vol. 1679, Springer.
Bzostek, Andrew et al., "An automated system for precise percutaneous access of the renal collecting system," Proceedings of the First Joint Conference on Computer Vision, Virtual Reality and Robotics in Medicine and Medial Robotics and Computer-Assisted Surgery, Lecture Notes in Computer Science, 1997, pp. 299-308, vol. 1205, Springer-Verlag.
Bzostek, Andrew, "Image Guided Percutaneous Pattern Placement in Soft Tissue," The Johns Hopkins University Dept. of Computer Science: Baltimore, 1997, pp. 2007-01-22.
Cadeddu, Jeffrey A. et al., "A Robotic System for Percutaneous Renal Access," The Journal of Urology, 1997; pp. 1589-1593, vol. 158—Issue 4.
Cadeddu, Jeffrey et al., "A robotic system for percutaneous renal access incorporating a remote center of motion design," Journal of Endourolog, 1998, S237, vol. 12.
Cannon, Jeremy W. et al., "Real-time three-dimensional ultrasound for guiding surgical tasks," Computer Aided Surgery, 2003, pp. 82-90, vol. 8—No. 2, John Wiley & Sons.
Cao, Caroline L., et al., "Task and motion analysis in endoscopic surgery," Submitted for Fifth Annual Symposium on Haptic Interfaces for Virtual Environment and Teloperator Systems for the Winter Meeting of ASME, 1996, pp. 1-32.
Carr, J., "Surface reconstruction in 3D medical imaging," PhD Thesis, Part 1, University of Canterbury, Christchurch, New Zealand, 1996, 112 Pages.
Carr, J., "Surface reconstruction in 3D medical imaging," PhD Thesis, Part 2, University of Canterbury, Christchurch, New Zealand, 1996, 112 Pages.
Cash, David M. et al., "Incorporation of a laser range scanner into an image-guided surgical system," The International Society for Optical Engineering (SPIE), Medical Imaging 2003: Visualization, Image-Guided Procedures, and Display; San Diego, CA, Ed. Robert L. Galloway, 2003, pp. 269-280, vol. 5029.

(56) References Cited

OTHER PUBLICATIONS

Chang, Jun Keun et al., "Intravascular micro active catheter for minimal invasive surgery," 1st Annual International Conference on Microtechnologies in Medicine and Biology, 2000, pp. 243-246.
Chen, Homer H. "A Screw Motion Approach to Uniqueness Analysis of Head-Eye Geometry," Computer Vision and Pattern Recognition, 1991, pp. 145-151, IEEE.
Chinzei, Kiyoyuki et al., "MR Compatible Surgical Assist Robot: System Integration and Preliminary Feasibility Study," in Proceedings of Third International Conference on Medical Imaging and Computer Assisted Surgery (MICCAI), 2000, pp. 921-930, vol. 1935, Springer-Verlag.
Choti, Michael A. et al., "Trends in Long Term Survival Following Liver Resection for Hepatic Colorectal Metastases," Ana Surg, 2002, pp. 759-766, vol. 235—No. 6, Lippincott Williams & Wilkins.
Choti, Michael A., "Hepatic Radiofrequency Ablation," Cancer Journal, 2000, pp. S291-S292, vol. 6—issue 4, Jones and Bartlett.
Choti, Michael A., "Surgical Management of Hepatocellular Carcinoma: Resection and Ablation," Journal of Vascular and Interventional Radiology, 2002, pp. S197-S203, vol. 13—No. 9.
Christensen, B. et al., "Model based sensor directed remediation of underground storage tanks," International Conf. on Robotics and Automation, Sacramento, CA, Apr. 1991, pp. 1377-1383, vol. 2. IEEE.
Christoforou, E.G. et al., "Robotic Arm for Magnetic Resonance imaging Guided Interventions," 1st IEEE/RAS-EMBS International Conference on Biomedical Robotics and Biomechatronics, Feb. 20-22, 2006, pp. 911-916.
Chung, Mathew et al., "Laparascopic Radiofrequency Ablation of Unresectable Hepatic Malignancies," Surg Endosc, 2001, pp. 1020-1026, vol. 15—No. 9, Springer-Verlag.
Cleary, Kevin et al., "State of the Art in Surgical Robotics:Clinical Applications and Technology Challenges," Computer Aided Surgery, 2001 [retrieved on Feb. 24, 2002], pp. 1-26.
Cleary, Kevin et al., "State of the art surgical robotics clinical applications and technology challenges," Computer Aided Surgery, 2001, pp. 312-328, vol. 6; Part 6, John Wiley & Sons.
Cleary,K. et al., "Robotically-assisted spine nerve blocks," Radiology, 2001, 1 pages, vol. 221—No. 618.
Colgate, Edward, J., "Power and Impedance Scaling in Bilateral Manipulation," IEEE International Conference on Robotics and Automation, Sacramento, California, Apr. 1991, pp. 2292-2297, vol. 3, IEEE.
D'Angelica M., "Staging Laparoscopy for Potentially Respectable Noncolorectal," Ann Surg Oncol, 2002, pp. 204-209, vol. 9—No. 2, Lippincott Williams & Wilkins.
Daniilidis, Konstantinos, Hand-Eye Calibration Using Dual Quaternions, Int. J. of Robotics Research, 2000, pp. 286-298, vol. 19—No. 3, Sage Publications, Inc.
Davies, Brain L. et al., "A Robotic system for tkr surgery," Proceedings of 3rd Annual North American Program on Computer Assisted Orthopaedic Surgery (CAOS USA), University of Pittsburgh Medical Center, Pittsburgh, Pennsylvania,published in Computer Aided Surgery, Jun. 17-19, 1999, p. 339, vol. 4—Iss. 6.
Davies, S. C.et al., "Ultrasound quantitaion of respiratory organ motion in the upper abdomen," British Journal of Radiology, 1994, pp. 1096-1102, vol. 37—Iss. 803.
De Cunha, D. et al., The MIDSTEP System for Ultrasound guided Remote Telesurgery, Proceedings of the 20th Annual International Conference of the IEEE Engineering in Medicine and Biology Society, 1998, pp. 1266-1269, vol. 3—No. 29, IEEE.
Debus, Thomas et al., "Multichannel Vibrotactile Display for Sensory Substitution During Teleoperation," Proc. SPIE Telemanipulator and Telepresence Technologies VIII, 2001, pp. 42-49, vol. 4570, SPIE.
Degoulange, E. et al., "HIPPOCRATE: an intrinsically safe robot for medical applications," IEEE/RSH International Conference on Intelligent Biomedicine, 1998, pp. 959-964, vol. 2, IEEE.
Delgorge, Cecile et al., "A Tele-Operated Mobile Ultrasound Scanner Using a Light-Weight Robo," IEEE Transactions on Information Technology in Biomedicine, 2005, pp. 50-58, vol. 9 No. 1, IEEE.
Dewan, Maneesh et al., "Vision-Based Assistance for Ophthalmic Micro-Surgery," Proceedings of Seventh International Conference on Medical Image Computing and Computer-Assisted Intervention (MICCAI), 2004, pp. 49-57, vol. 3217, Springer-Verlag.
Dodds, Zachary et al., "A hierarchical architecture for vision-based robotic manipulation tasks," in Proceedings of the International Conference on Vision Systems, 1999, pp. 312-330, vol. 542, Springer-Verlag.
Doggett, Stephen W., "Image Registered Real Time Intra- Operative Treatment Planning: Permanent Seed Brachytherapy," 2000, pp. 4.
Dolan, J.M. et al., "A Robot in an Operating Room: A Bull in a China Shop," 1987, pp. 1096-1097, vol. 2.
Elder, Matthew C. et al., "Specifying user interfaces for safety critical medical systems," Second Annual International Symposium on Medical Robotics and Computer Assisted Surgery, Nov. 1995, pp. 148-155.
Eldridge, B. et al., "A Remote Center of Motion Robotic Arm for Computer Assisted Surgery," Robotica, 1996, pp. 103-109, vol. 14 Issue 1.
Ellsmere, James et al., "A navigation system for augmenting laparoscopic ultrasound," Medical Image Computing and Computer-Assisted Intervention, Lecture Notes in Computer Science, 2003, pp. 184-191, Springer.
Fattal, Lischinsk, "Variational Classification for Visualization of 3D Ultrasound Data," Proceedings of the conference on Visualization, 2001, pp. 403-410, IEEE Computer Society.
Fenster, Aaron, et al., "3-D Ultrasound Imaging:A Review," IEEE Engineering and Medicine and Biology Magazine, Nov.-Dec. 1996, pp. 41-51, vol. 15—Issue 6, IEEE.
Fenster, Aaron, et al., "Three-dimensional ultrasound imaging of the prostate," SPIE International Symposium on Medical Imaging,San Diego, California,Published in SPIE: Medical Physics, Feb. 20-26, 1999, pp. 2-11, vol. 3859, SPIE.
Fichtinger, Gabor et al., "Robotically Assisted Percutaneous Local Therapy and Biopsy," 10th International Conference of Advance Robotics, 2001, pp. 133-151, IEEE.
Fichtinger, Gabor et al., "Transrectal prostate biopsy inside closed MRI scanner with remote actuation under real-time image guidance," Medical Image Computing and Computer-Assisted Intervention, Lecture Notes in Computer Science, 2002, pp. 91-98, vol. 2488, Springer Verlag.
Fichtinger, Gabor et al., "Surgical CAD/CAM and its application for robotically assisted percutaneous procedures," 30th Applied Imagery Pattern Recognition Workshop (AIPR), 2001, pp. 3-8, IEEE.
Fichtinger, Gabor et al., "System for Robotically Assisted Prostate Biopsy and Therapy With intraOperative CT Guidance," Journal of Academic Radiology, 2002, pp. 60-74, vol. 9 No. 1, Elsevier.
Fisher, Scott S., "Virtual interface environment," IEEE/A1AA 7th Digital Avionics Systems Conference Ft. Worth Texas, 1986, pp. 346-350, IEEE.
Frantz D.D et al., "Accuracy assessment protocols for electromagnetic tracking systems," Physics in Medicine and Biology, 2003, pp. 2241-2251, Issue 48.
Fu, K.S. et al., "Robotics: control, sensing, vision, and intelligence," 1987, pp. 12-76 and 201-265, Ch. 2 & 5, McGraw-Hill Book Company.
Fuchs, Henry et al., "Augmented Reality Visualization for Laparoscopic Surgery," Medical Image Computing and Computer-Assisted Intervention, 1998, pp. 934-943, vol. 1496, Springer-Verlag.
Fukuda, Toshio et al., "A new method of master-slave type of teleoperation for a micro-manipulator system," IEEE Microrobots and Teleoperations Workshop, 1987, 5 pages, IEEE.
Funda, Janez, "An experimental user interface for an interactive surgical robot," In 1st International Symposium on Medical Robotics and Computer Assisted Surgery (MRCAS 94), Pittsburgh, 1994, pp. 196-201, 203.
Funda, Janez et al., "Comparison of two manipulator designs for laparoscopic surgery," SPIE International Symposium on Optical

(56) References Cited

OTHER PUBLICATIONS

Tools for Manufacturing and Advanced Automation, 1994, pp. 172-183, vol. 2351, Telemanipulator and Telepresence Technologies.
Funda, Janez et al., "Constrained Cartesian Motion Control for Teleoperated Surgical Robots," IEEE Transactions on Robotics and Automation, IEEE, Jun. 1996, vol. 12, No. 3, pp. 453-465.
Funda, Janez et al., "Control and evaluation of a 7-axis surgical robot for laparoscopy," IEEE Int. Conf. on Robotics and Automation, 1995, pp. 1477-1484, vol. 2, IEEE.
Funda, Janez et al., "Image-Guided Command and Control of a Surgical Robot," Proc. Medicine Meets Virtual Reality II, 1994, pp. 52-57.
Funda, Janez et al., "Optimal Motion Control for Teleoperated Surgical Robots," Intl. Symp. on Optical Tools for Manuf. & Adv Autom,Telemanipulator Technology and Space Telerobotics, 1993, pp. 211-222, vol. 2057, SPIE.
Furuta, Katsuhisa et al., "Master slave manipulator based on virtual internal model following control concept," IEEE Intl. Conference on Robotics and Automation, 1987, pp. 567-572, vol. 1, IEEE.
Ganssle J.G.,,A Guide to Debouncing,The Ganssle Group,Jun. 2008,26 pages.
Garrett, William F. et al., "Real-Time Incremental Visualization of Dynamic Ultrasound Volumes Using Parallel BSP Trees," IEEE Proceedings Visualization, 1996, pp. 235-240, 490, IEEE.
Gee, Andrew et al., "Processing and visualizing three-dimensional ultrasound data," Journal of Radiology, 2004, pp. 186-193, vol .77.
Gelb, A., et al., Table of Contents for"Applied Optimal Estimation," The Analytic Science Corporation, MIT Press, Cambridge, Massachusetts,1974, 4 pages.
Gennari, G. et al., "Probabilistic data association methods in visual tracking of groups," IEEE Conference on Computer Vision and Pattern Recognition, 2004, pp. I-790-1-797, vol. 1—issue. 27, IEEE.
Gigot, Jean-Francois et al., "Laparoscopic Liver Resection for Malignant Liver Tumors Prclimary Results of a Multicenter European Study," Ann Surg, 2002, pp. 90-97, vol. 236—issue 1.
Gonzales, Adriana Vilchis et al., "A System for Robotic Tele-echography," Medical Image Computing and Computer-Assisted Intervention, 2001, pp. 326-334, vol. 2208, Springer.
Green, Philip, S. et al., "Mobile telepresence surgery," 2nd Annual Intl Symposium on Med. Robotics and Computer Assisted Surgery, Maryland Nov. 1995, pp. 97-103.
Grimson, W. Eric et al., "Automated Registration for Enhanced Reality Visualization in Surgery," 1st International Symposium on Medical Robotic and Computer Assisted Surgery (MRCAS), Pittsburgh, 1994, pp. 82-89.
Grimson, W.E.L., et al., "An automatic registration method for frameless stereotaxy, image guided surgery, and enhanced reality visualization," IEEE Transactions on Medical Imaging, vol. 15, No. 2, Apr. 1996, pp. 129-140.
Hager, Gregory D., "A Modular System for Robust Hand Eye Coordination Using Feedback from Stereo Vision," IEEE Transactions on Robotics and Automation, 1997, pp. 582-595, vol. 13—issue(4), IEEE.
Hager, Gregory D. et al., "Efficient Region Tracking With Parametric Models of Geometry and Illumination," IEEE Transactions on Pattern Analysis and Machine Intelligence, 1998, pp. 1025-1039, vol. 20—issue. 10, IEEE.
Hager Gregory D. et al., "Multiple Kernel Tracking with SSD," Proceedings of the IEEE Conference on Computer Vision and Pattern Recognition (CVPR 2004), 2004, pp. 1-790-1-797, vol. 1—issue 27, IEEE.
Hager, Gregory D. et al., "The XVision System: A Portable Substrate for Real Time Vision Applications," 1998, pp. 23-37, vol. 69—issue 1.
Hannaford, Blake et al., "Experimental and simulation studies of hard contact in force reflecting teleoperation," IEEE International Conference on Robotics and Automation Proceedings, 1988, pp. 584-589, vol. 1, IEEE.

Hannaford, Blake et al., "Performance Evaluation of a Six-Axis Generalized Force-Reflecting Teleoperator," IEEE Transactions on Systems, Man, and Cybernetics, 1991, pp. 620-633, vol. 21—No. 3, IEEE.
Harris, S.J. et al., "A robotic procedure for transurethral resection of the prostate," Second Annual International Symposium on Medical Robotics and Computer Assisted Surgery, 1995, pp. 264-271.
Harris, S.J. et al., "Experiences with Robotic Systems for Knee Surgery," First Joint Conference of CVRMed and MRCAS. Mar. 19-22, 1997, Grenoble, France; Springer, 1997, pp. 757-766.
Herline, Alan J. et al., "Image-Guided Surgery: Preliminary Feasibility Studies of Frameless Stereotactic Liver Surgery," Archives of Surgery, 1999, pp. 644-650, vol. 134—No. 6.
Herline, Alan J. et al., "Surface Registration for Use in Interactive," Image-Guided Liver Surgery, Computer Aided Surgery, 2000, pp. 11-17, vol. 5—No. 2.
Herman, Barry C., et al, "Telerobotic surgery creates opportunity for augmented reality surgery," Abstract No. T1F2, Telemedicine Journal and E-Health, vol. 11, Issue 2, p. 203, Apr. 2005.
Herman, Barry C., "On the Role of Three Dimensional Visualization for Surgical Applications in Interactive Human Machine Systems," Masters of Science Thesis in Computer Science, The Johns Hopkins University, Baltimore, 2005, 216 pages.
Herper Matthew, "Watch a $1.5 Million Surgical Robot Play a Board Game," Forbes. Apr. 12, 2011. 2 pages, Online [Available: http://www.forbes.com/sites/matthewherper/2011/04/12/watch-a-1-5-million-surgical-robot-play-a-board-game/#587224f011f5] Accessed Jun. 7, 2016.
Hespanha J.P. et al., "What Tasks Can Be Performed with an Uncalibrated Stereo Vision System", International Journal of Computer Vision, 1999, pp. 65-85, vol. 35—issue. (1).
Hill, John W., "Telepresence surgery demonstration system," Robotics and Automation, 1994, pp. 2302-2307, vol. 3, SRI International.
Ho, S. C.et al., "Robot Assisted Knee Surgery," IEEE Engineering in Medicine and Biology Magazine, 1995, pp. 292-300, vol. 14—Iss. 3, IEEE.
Hong, Jae-Sung et al., "A Motion Adaptable Needle Placement Instrument Based on Tumor Specific Ultrasonic Image Segmentation," Fifth International Conference on Medical Image Computing and Computer Assisted Intervention, MICCAI '02, Tokyo, Japan, Jul. 2002, pp. 122-129.
Horn, Berthold K.P., "Closed-form solution of absolute orientation using unit quaternions," Journal of the Optical Society of America A, vol. 4, No. 4, pp. 629-642, Apr. 1987.
Hunter, Ian W. et al., "A teleoperated microsurgical robot and associated virtual environment for eye surgery," Presence: Teleoperators and Virtual Environments, 1993, pp. 265-280, vol. 2—No. 4, MIt Press.
Hunter, Ian W. et al., "Ophthalmic microsurgical robot and associated virtual environment," Comput. Biol. Med, 1995, vol. 25, Issue 2, pp. 173-182, Pergamon.
Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.
Hutchinson, Seth et al., "A Tutorial Visual Servo Control," IEEE Transactions on Robotics and Automation, 1996, pp. 651-670, vol. 12 issue.5, IEEE.
IEEE Systems and Software Engineering—Recommended Practice for Architectural Description of Software-Intensive Systems, IEEE Std 1471-2000, 34 pages, First Edition, Jul. 15, 2007.
Inoue, Masao; "Six-Axis bilateral control of an articulated slave manipulator using a Cartesian master manipulator," Advanced robotics, 1990, pp. 139-150, vol. 4—Issue 2, Robotic society of Japan.
International Search Report and Written Opinion for Application No. PCT/US2012/064379, dated Mar. 29, 2013, 12 pages.
International Search Report and Written Opinion for Application No. PCT/US2012/064400, dated Mar. 27, 2013, 10 pages.
Intuitive Surgical, Inc., "Intuitive Surgical daVinci API v5.0 Reference Manual," generated Jul. 17, 2006, 149 pages.

(56) References Cited

OTHER PUBLICATIONS

Jackson, Bernie G. et al., "Force Feedback and Medical Simulation," Interactive Technology and the New Paradigm for Healthcare, Morgan et al. (Eds ), 1995, pp. 147-151, vol. 24, IOS Press and Ohms.

Jain, Ameet Kumar et al., "Understanding Bone Responses in B-mode Ultrasound Images and Automatic Bone Surface Extraction using a BayesianProbabilistic Framework," SPIE Medical Imaging, 2004, pp. 131-142, vol. 5373.

Johns Hopkins University and Intuitive Surgical, Inc., "System Requirements for the Surgical Assistant Workstation," Rev. 2, Jan. 29, 2007, 17 pages.

Jones D. B. et al., Chapter 25,"Next-Generation 3D Videosystems may Improve Laprascopic Task Performance," Interactive Technology and the New Paradigm for Healthcare, 1995, pp. 152-160.

Joskowicz, Leo et al., "Computers in Imaging and Guided Surgery," Computing in Science and Engineering, 2001, pp. 65-72, vol. 3—Issue: 5, IEEE.

Jurie, Frederic et al., "Hyperplane Approximation for Template Matching," IEEE Transactions on Pattern Analysis and Machine Intelligence(PAMI), 2002, pp. 996-1000, vol. 24—Issue 7, IEEE.

Kane, Robert A., "Intraoperative Ultrasonography, History, Current State of the Art, and Future Directions," J Ultrasound Med, 2004, pp. 1407-1420, vol. 23.

Kaplan, Irving, "Minimizing Rectal and Urinary Complications in Prostate Brachytherapy," Journal of Endourology, 2000, pp. 381-383.

Kapoor, Ankur and Russell H. Taylor, "A constrained optimization approach to virtual fixtures for multi-handed tasks," 2008 International Conference on Robotics and Automation (ICRA 2008), May 19-23, 2008, Pasadena, California, pp. 3401-3406.

Kapoor, Ankur et al., "Constrained Control for Surgical Assistant Robots," 2006 IEEE International Conference on Robotics and Automation (ICRA 2006), Orlando, Florida, May 15-19, 2006, pp. 231-236.

Kapoor, Ankur et al., "Simple Biomanipulation Tasks with a Steady Hand Cooperative Manipulator," In Proceedings of the Sixth International Conference on Medical Image Computing and Computer Assisted Intervention—MICCAI,, Lecture Notes in Computer Science, 2003, vol. 1, Springer.

Kapoor, Ankur et al., "Suturing in Confined Spaces: Constrained Motion Control of a Hybrid 8-DOF Robot," Proceedings, 12th International Conference on Advanced Robotics, 2005, pp. 452-459.

Kapoor, Ankur, Motion Constrained Control of Robots for Dexterous Surgical Tasks, Ph.D. Dissertation, The Johns Hopkins University, Department of Computer Science, Baltimore, Maryland, Sep. 2007, 351 pages.

Kato H., et al., "The Effects of Spatial Cues in Augmented Reality Video Conferencing," Hiroshima City University, Aug. 2001, 4 pages.

Kato H., et al. "Virtual Object Manipulation on a Table-Top AR Environment," Hiroshima City University, 2000, 9 pages.

Kavoussi, Louis R., "Laparoscopic donor nephrectomy," Kidney International, 2000, pp. 2175-2186, vol. 57.

Kazanzides, Peter et al., "A cooperatively-controlled image guided robot system for skull base surgery," Medicine Meets Virtual Reality 16 (MMVR 16) Conference, Jan. 30-Feb. 1, 2008, Long Beach, California, J.D. Westwood et al., eds., IOS Press, 2008, pp. 198-203.

Kazanzides, Peter et al., "Force Sensing and Control for a Surgical Robot," Int. Conference on Robotics and Automation, May 1992, Nice, France; pp. 612-617, vol. 1, IEEE.

Kazerooni, H. , "Human Extenders," ASME J. Dynamic Systems, Measurements and Control, 1993, pp. 281-290, vol. 115 No. 2(B).

Kazerooni, H., "Design and analysis of the statically balanced direct-drive robot manipulator," Robotics and Computer-Integrated Manufacturing, 1989, pp. 287-293, vol. 6, Issue 4.

Kazerooni, H. et al., "The Dynamics and Control of a Haptic Interface Device," IEEE Transactions on Robotics and Automation, 1994, pp. 453-464, vol. 10—Issue 4, IEEE.

Kazerooni, H., "Human/Robot Interaction via the Transfer of Power and Information Signals Part I: Dynamics and Control Analysis," IEEE International Conference on Robotics and Automation, 1989, pp. 1632-1640, IEEE.

Kilmer, R. D. et al., "Watchdog safety computer design and implementation," RI/SME Robots 8 Conference, Jun. 1984, pp. 101-117.

Kim, Won S. et al., "Active compliance and damping in telemanipulator control," Jet Propulsion Laboratory New technology Report, 1991, pp. 1-14a. vol. 15—Issue 4, JPL & NASA Case No. NP0-1796917466, Item 40.

Kitagawa, Masaya et al., "Effect of Sensory Substitution on Suture Manipulation Forces for Surgical Teleoperation," 12th Annual Medicine Meets Virtual Reality Conference, 2005, 8 pages.

Koizumi, Naoshi et al., "Development of Three-Dimensional Endoscopic Ultrasound System with Optical Tracking," Medical Image Computing and Computer-Assisted Intervention—MICCAI '02, Tokyo, 2002, pp. 60-65, vol. 2488, Springer-Verlag.

Koizumi, Norihiro et al., "Continuous Path Controller of Slave Manipulator in Remote Ultrasound Diagnostic System," Int. Conference on Robotics and Automation (ICRA 2002), 2002, pp. 3368-3373, vol. 4, IEEE.

Komada, Satoshi et al., "Bilateral robot hand based on estimated force feedback," IEEE Proceedings IECON 87 Cambridge MA, Nov. 3-6, 1987, pp. 602-607, vol. 2, IEEE.

Kon, Ryan et al., "An open-source ultrasound calibration toolkit," Medical Imaging Ultrasonic Imaging and Signal Processing, 2005, pp. 516-523, vol. 5750, SPIE.

Korein James U. et al., "A Configurable System for Automation Programming and Control," IEEE Conf. on Robotics and Automation. San Francisco, 1986, pp. 1871-1877, vol. 3, IEEE.

Kosugi, Yukio et al., "An articulated neurosurgical navigation system using MRI and CT Images," IEEE Transactions on Biomedical Engineering, 1988, pp. 147-152, vol. 35—Issue 2, IEEE.

Kragic D. et al., "Human-Machine Collaborative Systems for Microsurgical Applications," International Symposium on Robotics Research, 2005, pp. 731-741, vol. 24–Issue 9, Sage Publications.

Kruchten, Philippe B., "The 4+1 View Model of Architecture," IEEE Software, vol. 12, Issue 6, pp. 42-50, Nov. 1995.

Krupa, A. et al., "Automatic 3-D Positioning of Surgical Instruments during Laparoscopic Surgery Using Automatic Visual Feedback," Proceedings of the 5th International Conference on Medical Image Computing and Computer-Assisted Intervention-Part , Lecture Notes in Computer Science, 2002, pp. 9-16, vol. 2488, Springer Verlag.

Kumar, Rajesh, "An Augmented Steady Hand System for Precise Micromanipulation," 2001, 109 pages.

Kumar, Rajesh et al., "An Augmentation System for Fine Manipulation," Proceedings of the Third International Conference on Medical Image Computing and Computer-Assisted Intervention, Lecture Notes in Computer Science, 2000, pp. 956-964, vol. 1935, Springer Verlang.

Kumar, Rajesh et al., "Application of Task-Level Augmentation for Cooperative Fine Manipulation Tasks in Surgery," Proceedings of the 4th International Conference on Medical Image Computing and Computer-Assisted Intervention, Lecture Notes in Computer Science, 2001, pp. 1417-1418, vol. 2208, Springer Verlang.

Kumar, Rajesh et al., "Experiments with a Steady Hand Robot in Constrained Compliant Motion and Path Following", 1999, pp. 92-97, IEEE.

Kumar, Rajesh et al., "Preliminary Experiments in Cooperative Human/Robot Force Control for Robot Assisted Microsurgical Manipulation," Conference on Robotics and Automation, 2000, pp. 610-617, vol. 1, IEEE.

Kumar, Rajesh et al., "Preliminary experiments in robot/human microinjection," IEEE/RSJ International Conference on Intelligent Robots and Systems, 2003, pp. 3186-3191, vol. 3, IEEE.

Kwoh, Yik, San et al., "A Robot With Improved Absolute Positioning Accuracy for CT Guided Stereotactic Brain Surgery," IEEE Transactions on Biomedical Engineering, Feb. 1988, pp. 153-160, vol. 35—Issue 2, IEEE.

(56) References Cited

OTHER PUBLICATIONS

Lacroute, Philippe G., "Fast Volume Rendering Using a Shear-Warp Factorization of the Viewing Transformation PhD Thesis," Computer Science, Stanford, California, 1995, 236 Pages.

Lang, Samuel J., Xvision 2—A Framework for Dynamic Vision. Masters Thesis, Computer Science, Johns Hopkins University, Baltimore, 2001, pp. 1-49.

Lange, Thomas et al., Augmenting Intraoperative 3D Ultrasound with Preoperative Models for Navigation in Liver Surgery, Medical Image Computing and Computer-Assisted Interventions, 2004, pp. 534-541, vol. 3217, Springer Verlag.

Lau, William W. et al., "Stereo-Based Endoscopic Tracking of Cardiac Surface Deformation," Proceedings of Seventh International Conference on Medical Image Computing and Computer-Assisted Intervention (MICCAI), Lecture Notes in Computer Science, 2004, pp. 494-501, vol. 2, Springer Verlag.

Lavonius, Maija I. et al., "Staging of Gastric Cancer: A Study with Spiral Computed Tomography,Ultrasonography, Laparoscopy, and Laparoscopic Ultrasonography," Surgical Laparoscopy, Endoscopy & Percutaneous Techniques, 2002, pp. 77-81, vol. 12—No. 2, Lippincott Williams & Wilkins, Inc.

Lawson, Charles L. et al., "Linear least squares with linear inequality constraints Solving Least Squares Problems," 1974, pp. 158-173, Prentice Hall Inc.

Lazarevic, Zoran, "Feasibility of a Stewart Platform with Fixed Actuators as a Platform for CABG Surgery Device," 1997, 45 pages, Master's Thesis Columbia University Department of Bioengineering.

Lee Jr, Fred T. et al., "CT-monitored percutaneous cryoablation in a pig liver model," Radiology, 1999, pp. 687-692, vol. 211(3).

Leven, Joshua, "A Telerobotic Surgical System With Integrated Robot-Assisted Laparoscopic Ultrasound Capability," Thesis for Master of Science in Engineering in Computer Science, The Johns Hopkins University, Baltimore, Maryland, May 2005, 63 pages.

Leven, Joshua et al. "DaVinci Canvas: A Telerobotic Surgical System with Integrated, Robot-Assisted, Laparoscopic Ultrasound Capability," Medical Image Computing and Computer-Assisted Intervention (MICCAI), Lecture Notes in Computer Science, J. Duncan et al. Eds., Palm Spring, Springer Verlag, 2005, vol. 3749, pp. 811-818.

Levoy, Marc, "Display of Surfaces from Volume Data," IEEE Computer Graphics and Applications, 1988, pp. 29-37, vol. 8—lss. 3, IEEE.

Li, M., "Intelligent Robotic Surgical Assistance for Sinus Surgery," Ph.D. Dissertation, Johns Hopkins University, Baltimore, Aug. 2005, 246 pages.

Li, Ming and Russell H. Taylor, "Spatial Motion Constraints in Medical Robots Using Virtual Fixtures Generated by Anatomy," IEEE International Conference on Robotics and Automation, New Orleans, Apr. 2004, pp. 1270-1275.

Li, Ming and Russell H. Taylor, "Performance of surgical robots with automatically generated spatial virtual fixtures," IEEE International Conference on Robotics and Automation, Barcelona, Spain, Apr. 2005, pp. 217-222.

Li, Ming et al, "A Constrained Optimization Approach to Virtual Fixtures," IEEE/RSJ International Conference on Intelligent Robots and Systems (IROS 2005), Edmonton, Alberta, Canada, Aug. 2-6, 2005, pp. 1408-1413.

Li, Ming et al., "Optimal Robot Control for 3D Virtual Fixture inConstrained ENT Surgery," Proceedings of the Sixth International Conference on Medical Image Computing and Computer Assisted Intervention—MICCAI, Lecture Notes in Computer Science, 2003, pp. 165-172, vol. I, Springer Verlag.

Li, Ming et al., "Recognition of Operator Motions for Real-Time Assistance using Virtual Fixtures, IEEE," HAPTICS 2003, 11th Symposium on Haptic Interfaces for Virtual Environment and Teleoperator Systems, Mar. 22-23, 2003, pp. 125-131, IEEE.

Loser, Michael H. et al.. "A New Robotic System for Visually Controlled Percutaneous Interventions under CT Fluoroscopy," Medical Image Computing and Computer-Assisted Interventions,Lecture Notes in Computer Science, 2000, pp. 887-896, vol. 1935, Springer Verlag.

Loser, Michael H. et al., "Visual servoing for automatic and uncalibrated percutaneous procedures," SPIE Medical Imaging, 2000, pp. 270-281, vol. 3976, SPIE.

Madhani, Akhil J., "Design of Teleoperated Surgical Instruments for Minimally Invasive Surgery," Feb. 1998, pp. 1-251.

Maehara, S. et al., "Laparoscopy-Assisted Hepatectomy Using the Endoclose," Surg Endosc, 2002, pp. 1362-1365, vol. 16(9), Springer Verlag.

Maier, Georg, E. et al., "A Dynamically Configurable General Purpose Automation Controller," Proceedings of IFAC/IFIP Symp. on Software for Computer Control, 1986, pp. 47-52, Pergamon Press.

Mala, T. et al., "A Comparative Study of the Short-Term Outcome Following Open and Laparoscopic Liver Resection of Colorectal Metastases," Surg Endosc, 2002, pp. 1059-1063, vol. 16(7), Springer Verlag.

Marayong, Panadda et al., "Spatial Motion Constraints: Theory and Demonstrations for Robot Guidance Using Virtual Fixtures," IEEE International Conference on Robotics and Automation Robotics and Automation, 2003, pp. 1954-1959, vol. 2, No. 14-19, IEEE.

Marescaux, Jadques and Francesco Rubino, "Virtual Operative Fields for Surgical Simulation," Chapter 4 in Primer of Robotic & Telerobotic Surgery, Eds. Garth H. Ballantyne et al., Pub. By Lippincott Williams & Wilkins, Philadelphia, 2004, pp. 26-31.

Masamune K., et al., "Development of a MRI Compatible Needle Insertion Manipulator for Stereotactic Neurosurgery," Journal of Image Guided Surgery, 1995, vol. 1, pp. 242-248.

Masamune, Ken et al., "Development of a MRI Compatible Needle Insertion Manipulator for Stereotactic Neurosurgery," Image Guid Surg, 1995, pp. 165-172.

Masamune Ken et al., "Development of CT-PAKY frame system—CT image guided needle puncturing manipulator and a single slice registration for urological surgery," Proc. 8th annual meeting of Japanese Society for Computer Aided Surgery (JSCAS), 1999, pp. 89-90.

Masamune, Ken et al., "System for Robotically Assisted Percutaneous Procedures With Computed Tomography Guidance," Journal of Computer-Assisted Surgery, 2001, pp. 370-383, vol. 6—No. 6, Wiley-Liss, Inc.

Masamune, Ken H. et al., "A Newly Developed Stereotactic Robot with Detachable Drive for Neurosurgery," 1st International Conference on Medical Image Computing and Computer-Assisted Intervention—MICCAI,Cambridge, Massachusetts; Springer, Oct. 11-13, 1998, pp. 215-222, vol. 1496.

Massie, Thomas H. et al., "The Phantom Haptic Interface: A Device for Probing Virtual Objects," Proceedings of the ASME Winter Annual Meeting, Symposium on Haptic Interfaces for Virtual Environment and Teleoperator Systems, 1994, 7 pages.

Mayer, Hermann et al., "Skill Transfer and Learning by Demonstration in a Realistic Scenario of Laparoscopic Surgery," International Conference on Humanoids, 2003, 17 pages, IEEE.

Mayer, Hermann et al., "The Endo [PA]R System for Minimally Invasive Robotic Surgery," IEEE/RSJ International Conference on Intelligent Robots and Systems (IROS), 2004, pp. 3637-3642, vol. 4, IEEE.

Megali, Giusepp et al., "A Computer-Assisted Robotic Ultrasound-Guided Biopsy System for Video-Assisted Surgery," Proceedings of the 4th International Conference on Medical Image Computing and Computer-Assisted Intervention, Lecture Notes in Computer Science, 2001, pp. 343-350, vol. 2208, Springer-Verlag.

Menack, M. et al., "Staging of pancreatic and ampullary cancers for resectability using laparoscopy with laparoscopic ultrasound," Surg Endosc, 2001, pp. 1129-1134, vol. 15—No. 10, Springer-Verlag.

Menon, Mani, "Vattikuti Institute prostatectomy, a technique of robotic radical prostatectomy for management of localized carcinoma of the prostate: experience of over 1100 cases," Urol Clin N Am, 2004, pp. 701-717, vol. 31.

Merola, Stephen et al., "Comparison of Laparoscopic Colectomy With and Without the Aid of a Robotic Camera Holder," Surg

(56) References Cited

OTHER PUBLICATIONS

Laparosc Endosc Percutan Tech, 2002, pp. 45-61, vol. 12—No. 1, Lippincott Williams & Wilkins, Inc.
Michael B. Cohn's Home Page, http://ww-bsac.ees.berkeley.edu/users/michaelc/, downloaded Nov. 1, 1996, p. 1; UC Berkeley/Endorobotics Corporation Surgical Robotics Project Job Openings, http:/www-bsac.eecs.berkeley.edu/users/michaelc/jobs.html, downloaded Nov. 1, 1996, p. 1; and Medical Robotics, http://robotics.eecs.berkeley.edu/~mcenk/medical/, downloaded Nov. 1, 1996, pp. 1-8.
Migga, Michael I. et al., "Intraoperative Registration of the Liver for Image-Guided Surgery System," The International Society for Optical Engineering (SPIE), Medical Imaging 2003: Visualization, Image-Guided Procedures, and Display; San Diego, CA, Ed. Robert L. Galloway, 2003, pp. 350-359, vol. 5029.
Mitsuishi, Mamoru et al., "A tele-micro-surgery system with co-located view and operation points and a rotational-force-feedback-free master manipulator," 2nd Annual Intl. Symposium on Medical robotics and Computer Assisted Surgery Baltimore Maryland, Nov. 4-7, 1995, pp. 111-118.
Mitsuishi, Mamoru et al., "Remote Ultrasound Diagnostic System," Conf. on Robotics and Automation, 2001, pp. 1567-1574, vol. 2, IEEE.
Mourgues, Fabien et al., "Flexible Calibrations of Actuated Stereoscopic Endoscope for Overlay in Robot Assisted Surgery," Proceedings of the 5th International Conference on Medical Image Computing and Computer-Assisted Intervention—Part I, Lecture Notes in Computer Science, 2002, pp. 25-34, vol. 2488, Springer-Verlag.
Muratore, Diane M. et al., "Beam Calibration Without a Phantom for Creating a 3D Free-hand Ultrasound System," Ultrasound in Medicine and Biology, 2001, pp. 1557-1566, vol. 27—No. 11, Elsevier.
Nakakura, Eric K et al., "Hepatocellular Carcinoma: Current Management Recommendations," Advances on Oncology, 2000, pp. 12-18, vol. 16—No. 2.
Neisius B. et al., "Robotic manipulator for endoscopic handling of surgical effectors and cameras," 1st Intl. Symposium on Medical Robotics and Computer Assisted Surgery, 1994, pp. 169-175, vol. 2.
Nelson, Thomas R. et al., "Interactive Acquisition, Analysis, and Visualization of Sonographic Volume Data," International Journal of Imaging Systems and Technology, 1997, pp. 26-37, vol. 8, John Wiley & Sons, Inc.
Nelson, Thomas, R. et al., "Three-dimensional ultrasound imaging," Ultrasound in Medicine & Biology, 1998, pp. 1243-1270, vol. 24—No. 9, Elsevier.
Ng, W.S. et al., "Robotic Surgery, A First-Hand Experience in Transurethral Resection of the Prostate," IEEE Engineering in Medicine and Biology, Mar 1993, pp. 120-125, vol. 12—Issue 1, IEEE.
Novotny Paul M. et al., "Tool Localization in 3D Ultrasound Images," Medical Image Computing and Computer-Assisted Intervention, 2003, pp. 969-970, vol. 2879, Springer.
Office Action dated May 1, 2012 for Japanese Application No. 20090518470 filed Jun. 22, 2007, 7 pages.
Office Action dated Jan. 26, 2015 for Japanese Application No. 20130186992 filed Sep. 10, 2013, 9 pages.
Office Action dated Jun. 12, 2015 for Japanese Application No. 20130186992 filed Sep. 10, 2013, 8 pages.
Ohbuchi, Ryutarou et al., "Incremental Volume Reconstruction and Rendering for 3D Ultrasound Imaging," The International Society of Optical Engineering, 1992, pp. 312-323, vol. 1808, SPIE.
Park, Shinsuk et al., "Virtual Fixtures for Robotic Cardiac Surgery," Proceedings of the 4th International Conference on Medical Image Computing and Computer-Assisted Intervention, 2001, pp. 1419-1420, vol. 2208, Springer-Verlag.
Patriciu Alexandru et al., "Motion-based robotic instrument targeting under c-arm fluoroscopy," Medical Image Computing and Computer-Assisted Interventions, 2000, pp. 988-998, vol. 1935, Springer.

Paul, Howard A. et al., "Development of a Surgical Robot for Cementless Total Hip Arthroplasty," Clinical Orthopaedics, Dec. 1992, pp. 57-66, vol. 285.
PCT/US07/71850 International Search Report and Written Opinion of the International Searching Authority, dated Feb. 13, 2009, 9 pages.
PCT/US09/46234 International Search Report and Written Opinion of the International Searching Authority, dated Sep. 9, 2009, 13 pages.
PCT/US09/56078 International Search Report and Written Opinion of the International Searching Authority, dated Jan. 20, 2010, 12 pages.
PCT/US10/28886 International Search Report and Written Opinion of the International Searching Authority, dated Jul. 6, 2010, 11 pages.
PCT/US10/28897 International Search Report and Written Opinion of the International Searching Authority, dated Jul. 19, 2010, 16 pages.
PCT/US10/38246 International Search Report and Written Opinion of the International Searching Authority, dated Sep. 14, 2010, 17 pages.
PCT/US2011/036109 International Search Report and Written Opinion of the International Searching Authority, dated Oct. 19, 2011, 16 pages.
PCT/US2011/036109 Invitation to Pay Additional Fees and Partial International Search Report, dated Aug. 18, 2011, 5 pages.
Podnos, Yale, D. et al., "Laparoscopic Ultrasound with Radiofrequency Ablation in Cirrhotic Patients with Hepatocellular Carcinoma," Am Surg, 2001, pp. 1181-1184, vol. 67—No. 12.
Pose—definition from Merriam Webster Dictionary, 4 pages, [online], [retrieved on Apr. 3, 2015]. Retrieved from the Internet< URL: http://www.merriam-webster.com/dictonary/pose>.
Posture—definition from Merriam Webster Dictionary, 4 pages, [online], [retrieved on Apr. 3, 2015]. Retrieved from the Internet:< URL: http://www.merriam-webster.com/dictonary/posture>.
Poulose P. K et al., "Human vs Robotic Organ Retraction During Laparoscopic Nissen Fundoplication," Surgical Endoscopy, 1999, pp. 461-465, vol. 13, Springer-Verlag.
Prager Richard et al., "Practical segmentation of 3D ultrasound," In Proceedings of Medical Image Understanding and Analysis, 1999, pp. 161-164.
Prager Richard et al., "Rapid Calibration for 3D Freehand Ultrasound," Ultrasound in Medicine and Biology, 1998, pp. 855-869, vol. 24—No. 6, Elsevier.
Prasad, Srinivas K. et al., "A minimally invasive approach to pelvic osteolysis," 2002, in Proc. Computer-Assisted Orthopaedic Surgery (CAOS), pp. 349-350.
Prasad Srinivas K. et al., "A Modular 2-DOF Force-Sensing Instrument for Laparoscopic Surgery," Proceedings of the Sixth International Conference on Medical Image Computing and Computer Assisted Intervention—MICCAI,Lecture Notes in Computer Science, 2003, pp. 279-286, vol. I, Springer.
Pre-Appeal Examination Report, dated Sep. 3, 2014 for Japanese Application No. JP20120503535 filed Mar. 26, 2010, 7 pages.
Preising, B. et al., "A Literature Review: Robots in Medicine," IEEE Engineering in Medicine and Biology, 1991, pp. 13-22, 71, vol. 10—Issue 2, IEEE.
Ramey, N. A., "Stereo-Based Direct Surface Tracking with Deformable Parametric Models," Thesis submitted to the Johns Hopkins University, Maryland, Apr. 2003, 104 pages.
Ramey, Nicholas A. et al., "Evaluation of Registration Techniques in a robotic approach to pelvic osteolysis," International Proceedings of Computer Assisted Orthopaedic Surgery (CAOS), 2004, pp. 26-27.
Rasmussen, Christopher et al., "Probabilistic data association methods for tracking complex visual objects," IEEE Transactions on Pattern Analysis and Machine Intelligence, 2001, pp. 560-576, vol. 23, Issue 6, IEEE.
Ratner, Lloyd E. et al, "Laparoscopic live donor nephrectomy removes disincentives to live donation," Transplantation, 1997, pp. 3402-3403, vol. 29—Issue 8, Elsevier.
Ratner, Lloyd E. et al., "Laparoscopic live donor nephrectomy," Transplantation, 1995, pp. 1047-1049.

(56) References Cited

OTHER PUBLICATIONS

Rau, Beate, M. eta al., "Is There Additional Information From Laparoscopic Ultrasound in Tumor Staging", Digestive Surgery, 2002, pp. 479-483, vol. 19—No. 6.

Rockall, Timothy A., "The da Vinci Telerobotic Surgical System," Chapter 8 in Primer of Robotic & Telerobotic Surgery, Eds. Garth H. Ballantyne et al., Pub. By Lippincott Williams & Wilkins, Philadelphia, 2004, pp. 57-60.

Rohling, Robert et al., "Three-dimensional spatial compounding of ultrasound images," Medical Image Analysis, 1996, pp. 177-193, vol. 1—No. 3, Oxford University Press.

Rohling, Robert N. et al., "Radial basis function interpolation for 3-d ultrasound," CUED/F-INFENG/TR 327, Cambridge University, Jul. 1998, 28 Pages.

Rosen, Jacob et al., "The BlueDRAGON—A System for Measuring the Kinematics and the Dynamics of Minimally Invasive Surgical Tools In-Viva," Proceedings of the 2002 IEEE International Conference on Robotics 8 Automation, 2002, pp. 1876-1881, IEEE.

Rosenberg, Louis B., "Human interface hardware for virtual laparoscopic surgery," Proceedings of the Interactive Technology and the New Paradigm for Healthcare, 1995, pp. 322-325, Amsterdam: IOS Press.

Rosenberg, Louis B., "Virtual Fixtures: Perceptual Tools for Telerobotic Manipulation," IEEE Virtual Reality International Symposium, 1993, pp. 76-82, IEEE.

Rothbaum Daniel L. et al., "Robot-assisted stapedotomy: micropick fenestration of the stapes footplate," Otolaryngology—Head and NeckSurgery, 2002, pp. 417-426, vol. 127.

Rothbaum Daniel L. et al., "Task Performance in stapedotomy: Comparison between surgeons of different experience levels," Otolaryngology—Head and Neck Surgery, 2003, pp. 71-77, vol. 128—No. 1.

Roy, Jaydeep, "Advances in the design, analysis and control of force controlled robots," Master's Thesis, Mechanical Engineering, Johns Hopkins University, Baltimore, 2001, 210 Pages.

Sakas, Georgios et al., "Extracting surfaces from fuzzy 3D-Ultrasound data," Proceedings of the 22nd annual conference on Computer graphics and interactive techniques, 1995, pp. 465-474.

Salcudean, Septimiu E. et al., "A Robot System for Medical Ultrasound," 9th International Symposium of Robotics Research (ISRR'99), 1999, pp. 195-202.

Santambrogio, R. et al., "Ultrasound-Guided Interventional Procedures of the Liver During Laparoscopy: Technical Considerations," Surg Endosc, 2002, pp. 349-354, Springer-Verlag.

Sastry, Shankar et al., "Millirobotics for remote minamally invasive surgery," Proceedings of the Intl. Workshop on Some Critical Issues in Robotics, Singapore, Oct. 2-3, 1995, pp. 81-98.

Sastry, Shankar, http://robotics.eecs.berkeley.edu, Nov. 1, 1995, Total 8 pages.

Sastry, Shankar, "MilliRobotics in Minimally Invasive Telesurgery," Internet, http://robotics.eecs.berkeley.edu, 1996, 8 pages.

Schenker, Paul S. et al., "Development of a Telemanipulator for Dexterity Enhanced Microsurgery," 2nd Annual International Symposium on Medical Robotics and Computer Assisted Surgery, Nov. 4-7, Baltimore, Maryland, 1995, pp. 81-88.

Schorr, Oliver et al., "Distributed Modular Computer-Integrated Surgical Robotic Systems: Architecture for Intelligent Object Distribution," Proceedings of the Third International Conference on Medical Image Computing and Computer-Assisted Intervention, Lecture Notes in Computer Science, 2000, pp. 979-978, vol. 1935, Springer.

Schreiner, Steve et al., "A system for percutaneous delivery of treatment with a fluoroscopically-guided robot," Proceedings of the First Joint Conference on Computer Vision, Virtual Reality and Robotics in Medicine and Medial Robotics and Computer-Assisted Surgery,Lecture Notes in Computer Science, 1997, pp. 747-756, Springer-Verlag.

Schweikard, Achim et al., "Motion Planning in Stereotaxic Radiosurgery," IEEE Transactions on Robotics and Automation, 1993, pp. 909-916, vol. 1, IEEE.

Scott, D.J., "Accuracy and Effectiveness of Laparoscopic vs. Open Hepatic Radiofrequency Ablation," Surg Endosc, 2001, pp. 349-354, vol. 16—No. 2, Springer.

Shahram, Payandeh, et al., "On Application of Virtual Fixtures as an Aid for Telemanipulation and Training," IEEE 10th Symposium on Haptic Interfaces for Virtual Environment and Teleoperator systems, Mar. 24-25, 2002, pp. 18-23, IEEE.

Simaan, Nabil et al., "A Dexterous System for Laryngeal Surgery: Multi-Backbone Bending Snake-like Slaves for Teleoperated Dextrous Surgical Tool Manipulation," IEEE International Conference on Robotics and Automation, 2004, pp. 351-357, IEEE.

Simaan, Nabil et al., "High Dexterity Snake-Like Robotic Slaves for Minimally Invasive Telesurgery of the Upper Airway," MICCAI 2004—the 7th International Conference on Medical Image Computing and Computer-Assisted Intervention, 2004, pp. 17-24.

Solomon, S. B. et al., "Robotically Driven Interventions: A Method of Using CT Fluoroscopy without Radiation Exposure to the Physician," Radiology, 2002, vol. 225, pp. 277-282.

Solus-3D Ultrasound Project in Obstetrics and Gynaecology, University of Cambridge, http://mi.eng.cam.ac.uk/research/projects/Solus/, downloaded Jul. 5, 2007, 4 pages.

Sommer, Graham et al., "Liver tumors: utility of characterization at dual frequency US," Radiology, 1999, pp. 629-636, vol. 211—No. 3.

Steele, Micah R. et al., "Shared control between human and machine: using a haptic steering wheel to aid in land vehicle guidance," Human Factors and Ergonomics Society 45th Annual Meeting, Minneapolis, Minnesota, 2001, pp. 1671-1675.

Steen, Erik et al., "Volume Rendering of 3D Medical Ultrasound Data Using Direct Feature Mapping," IEEE Transactions on Medical Imaging, 1994, pp. 517-525, vol. 13—Iss. 3, IEEE.

Stefansic, James D. et al., "Registration of Physical Space to Laparoscopic Image Space for Use in Minimally Invasive Hepatic Surgery," IEEE Transactions on Medical Imaging, 2000, pp. 1012-1023, vol. 19—No. 10, IEEE.

Stetten, George D et al., "Overlaying Ultrasound Images on Direct Vision," Journal of Ultrasound in Medicine, 2001, pp. 235-240, vol. 20—No. 3.

Stewart, Charles V. et al., "The Dual-Bootstrap Iterative Closest Point Algorithm With Application to Retinal Image Registration," IEEE Transactions on Medical Imaging, Nov. 2003, pp. 1379-1394, vol. 22—No. 11, IEEE.

Stoainovici D., et al., "Robotic Telemanipulation for Percutaneous Renal Access," in 16th World Congress on Endourology, New York City, Sep. 3-6, 1998, Poster Session 17-5, p. S201.

Stoianovici, Dan, "A Modular Surgical Robotic System for Image Guided Percutaneous Procedures," Proceedings of the First International Conference on Medical Image Computing and Computer-Assisted Intervention, pp. 404-410, vol. 1496, Springer-Verlag, 1998.

Stoianovici, Dan et al., "Robotic for Precise Percutaneous Needle Insertion," In Thirteenth Annual Meeting of the Society for Urology and Engineering. San Diego, May 1998, pp. 4.

Stoll, Jeff, "Ultrasound-based servoing of manipulators for telesurgery," Telemanipulator and Telepresence Technologies VIII Conference, 2001, pp. 78-85, SPIE.

Sublett, John W. et al. "Design and implementation of a digital teleultrasound system for real-time remote diagnosis," 8th IEEE Symposium on Computer-Based Medical Systems, IEEE Computer Society Press, Jun. 9-10, 1995, pp. 292-298.

Suramo, I. et al., "Cranio-caudal movements of the liver, pancreas and kidneys in respiration," Acta Radiologica: Diagnosis, 1984, pp. 129-131, vol. 25, Radiological Societies.

Susil, Robert, C. et al., "A Single Image Registration Method for CT Guided Interventions," 2nd International Symposium on Medical Image Computing and Computer-Assisted Interventions (MICCAI' 99),Lecture Notes in Computer Science, 1999, pp. 798-808, vol. 1679, Springer-Verlag.

Szeliski, Richard, "Motion Estimation with Quadtree Splines," IEEE 5th International Conference on Computer Vision, 1995, pp. 757-763, vol. 18—Issue. 12, IEEE Computer Society Washington, DC, USA.

(56) References Cited

OTHER PUBLICATIONS

Taubes, Gary et al., "Surgery in Cyberspace," Discover magazine, Dec. 1994, vol. 15, issue 12, pp. 85-92.
Tavakoli, M., et al, A Force Reflective Master-Slave System for Minimally Invasive Surgery, Proc. IEEE/RSJ International Conference on Intelligent Robots and Systems, 2003, pp. 3077-3082, vol. 4, IEEE.
Taylor R.H., et al., Table of Contents, "Computer-Integrated Surgery," Technology and Clinical Applications, The MIT Press, Cambridge, MA,1996, 8 pages.
Taylor, Russell H., "A Perspective on Medical Robotics," Proceedings of the IEEE, vol. 94, No. 9, Sep. 2006, pp. 1652-1664.
Taylor, Russell H. "An Image-directed Robotic System for Precise Orthopaedic Surgery," IEEE Transactions on Robotics mid Automation, 1994, pp. 261-275, vol. 10—No. 3, IEEE.
Taylor, Russell H. and Christopher Hasser, "Development of a Surgical Assistant Workstation for Teleoperated Surgical Robots," NSF Proposal No. 0646678, Aug. 2006, 16 pages.
Taylor, Russell H. and Dan Stoianovici, "Medical Robotic Systems in Computer-Integrated Surgery," Problems in General Surgery, by Lippincott Williams & Wilkins, Inc., Philadelphia, Pennsylvania. vol. 20, No. 2, pp. 1-9, 2003.
Taylor, Russell H. and Peter Kazanzides, "Medical Robotics and Computer-Integrated Interventional Medicine," Chapter 18: Biomedical Information Technology, David Dagan Feng, Ed., Academic Press (Elsevier), 2008, pp. 393-416.
Taylor, Russell H. et al., "A Computational Architecture for Programmable Automation Research," Conference on Intelligent Robots and Computer Vision, 1986, pp. 438-440, vol. 726, SPIE.
Taylor, Russell H. et al., "A General Purpose Control Architecture for Programmable Automation Research," Proceedings of the Third International Symposium on Robotics, 1986, pp. 165-174, MIT Press.
Taylor, Russell, H et al., "A Steady-Hand Robotic System for Microsurgical Augmentation," International Journal of Robotics Research, 1999, pp. 1201-1210, vol. 18—No. 12, Springer-Verlag.
Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.
Taylor, Russell H. et al., "A Telerobotic System for Augmentation of Endoscopic Surgery," in IEEE Conference on Engineering in Medicine and Biology, vol. 14, 1992, pp. 1054-1056, vol. 3, IEEE.
Taylor, Russell, H et al., "AML a Manufacturing Language," The International Journal of Robotics Research, 1982, pp. 19-41, vol. 1—No. 3, SAGE Publications.
Taylor, Russell H. et al., "An Image-directed Robotic System for Hip Replacement Surgery," J. Robotics Society of Japan, 1990, pp. 615-620, vol. 8—issue 5.
Taylor, Russell, H. et al., "An Integrated Robot Systems Architecture," Proceedings of the IEEE, 1983, pp. 842-856, vol. 71—Issue 7, IEEE.
Taylor, Russell H., et al., "An overview of computer-integrated surgery at the IBM Thomas J. Watson Research Center," IBM J Research and Development, 1996, pp. 163-183, vol. 40, Issue 2, IBM Corp.
Taylor, Russell H., et al., "Chapter 46: A Telerobotic Assistant for Laparoscopic Surgery," in Computer-Integrated Surgery, R. H. Taylor, et al., Editors, 1996, MIT Press. pp. 581-592.
Taylor, Russell H. et al., "Computer-Integrated Revision Total Hip Replacement Surgery: Concept and Preliminary Results," 1999, Medical image analysis, pp. 301-319, vol. 3—Issue 3, Oxford University Press.
Taylor, Russell H. et al., "Medical Robotics and Computer-Integrated Surgery," Chapter 52 in Springer Handbook of Robotics, Springer, 2008, pp. 1199-1222.
Taylor, Russell H. et al., "Medical Robotics in Computer-Integrated Surgery," IEEE Transactions on Robotics and Automation, 2003, pp. 765-781, vol. 19—No. 5, IEEE.
Taylor, Russell, H. et al., "Redundant Consistency Checking in a Precise Surgical Robot," in 12'th Annual Conference on Engineering in Medicine and Biology, 1990, pp. 1933-1935, vol. 12—No. 5, IEEE.
Taylor, Russell H. et al., "Research Report: A Telerobotic Assistant for Laparoscopic Surgery," Accepted to IEEE EIMBS Magazine, Special Issue on "Robotics in Surgery," Dec. 1994, 24 pages.
Taylor, Russell, H et al., "The Architecture of an Integrated Robot System," First Int. Conf. on Advanced Robotics (ICAR)., 1983, pp. 389-398.
Taylor, Russell H. "Medical Robotics and Computer-Integrated Surgery," Handbook of Industrial Robotics, Second Edition, 1999, pp. 1213-1230, Chapter 65, John Wiley & Sons.
Taylor, Russell H. "Medical Robots," in Computer and Robotic Assisted Knee and Hip Surgery, 2004, pp. 54-59, Oxford Press.
Taylor, Russell H., "Robotics in Orthopedic Surgery," In Computer Assisted Orthopaedic Surgery (CAOS), L.P. Nolte and R. Ganz, Editors. 1999, Hogrefe and Huber, 1999, pp. 35-41.
Taylor, Russell H. "The Planning and Execution of Straight Line Manipulator Trajectories," IBM Journal of Research and Development, 1979, pp. 424-436, vol. 23—Issue 4.
Taylor, Russell H., "Ultrasound Assistant for a Laparoscopic Surgical Robot," NIH STTR Phase II Proposal R42-RR019159, revised May 2001, 54 pages.
Taylor, Russell H., Videotape: "Computer Assisted Surgery at IBM T. J. Watson Research Center," 22 minutes 10 seconds, 1994 and 1995.
Teistler, Michael et al., "Virtual Tomography: A New Approach to Efficient Human-Computer Interaction for Medical Imaging," Proc. of SPIE,, The International Society for Optical Engineering (SPIE), Medical Imaging 2003: Visualization, Image-Guided Procedures, and Display; San Diego, CA, Ed. Robert L. Galloway, 2003, pp. 512-519, vol. 5029.
Tewari, Ashutosh et al., "Technique of da Vinci Robot-Assisted Anatomic Radical Prostatectomy," Urology, 2002, pp. 569-72,vol. 60—No. 4, Elsevier.
The VolPack Volume Rendering Library, https://graphics.stanford.edu/software/volpack/, 1995, 4 pages.
Thring, M.W., Robots and Telechirs: Manipulators with Memory; Remote Manipulators; Machine Limbs for the Handicapped, Ellis Horwood Limited, England,1983, 79 pages, including Table of Contents, Preface, Chap. 5 (pp. 108-131), Chap. 7 (pp. 194-195, 235), Chap. 8 (pp. 236-287), Chap. 9 (p. 279).
Toon, John, "Virtual Reality for Eye Surgery," Georgia Tech Research News, 1993, 4 Pages.
Toyama, Kentaro et al., "Incremental Focus of Attention for Robust Vision-based Tracking," International Journal of Computer Vision, 1999, pp. 45-63, vol. 35—No. 1, Kluwer Academic Publishers.
Trevelyan, James P. et al., "Motion Control for a Sheep Shearing Robot," IEEE Robotics Research Conference, the 1st International Symposium, Carroll, NH, USA., 1983, pp. 175-190, in Robotics Research, MIT Press.
Trivedi, Mohan M. et al., "Developing telerobotic systems using virtual reality concepts," 1993 IEEE/RSJ International Conference on Intelligent Robots and systems, 1993, pp. 352-359, vol. 1, IEEE.
Troccaz, Jocelyne et al., "The use of localizers, robots, and synergistic devices in CAS," Proceedings of the First Joint Conference on Computer Vision, Virtual Reality and Robotics in Medicine and Medial Robotics and Computer-Assisted Surgery,Lecture Notes in Computer Science, 1997, pp. 727-736, vol. 1205, Springer-Verlag.
Umeyama, Shinji, "Least-Squares Estimation of Transformation Parameters between Two Point Patterns," IEEE Transactions on Pattern Analysis and Machine Intelligence (PAMI), vol. 13, No. 4, pp. 376-380, Apr. 1991.
U.S. Appl. No. 11/583,963 Non-Final Office Action dated Jul. 9, 2009, 40 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Vibet, C., "Properties of Master-Slave Robots," Motor-con, MOTORCON'87, Hannover, Apr. 1987, pp. 309-316.

(56) References Cited

OTHER PUBLICATIONS

Vilchis, Adriana et al., "A New Robot Architecture for Tele-Echography," IEEE Trans. Robotics & Automation, pp. 922-926, 2003, vol. 19—No. 5, IEEE.
Viswanathan, Anand et al., "Immediate Ultrasound Calibration with Three Poses and Minimal Image Processing," MICCAI, 2004, pp. 446-454, vol. 2, Springer-Verlag.
Webster Robert J. et al., "Design Considerations for Robotic Needle Steering," International Conference on Robotics and Automation, 2005, pp. 3588-3594, IEEE.
Webster Robert J. et al "Nonholonomic Modeling of Needle Steering," The International Journal of Robotics Research, 2004, pp. 509-525, vol. 25—No. 5-6, SAGE Publications.
Wei, Guo-Quing et al., "Real-Time Visual Servoing for Laparoscopic Surgery," IEEE Engineering in Medicine and Biology Magazine, Jan./Feb. 1997, pp. 40-45, vol. 16—Issue 1, IEEE.
Wei, Zhouping et al "Robot-assisted 3D-TRUS guided prostate brachytherapy: system integration and validation," Medical Physics, 2004, pp. 539-548, vol. 31—No. 3.
Wengert, C., "Camera Calibration Toolbox for Matlab," http://www.vision.caltech.edu/bouguetj/calib_doc/, downloaded Oct. 24, 2006, 9 pages.
Wilhelm, Dirk et al., "Electromagnetically Navigated Laparoscopic Ultrasound," Surg. Technol. Int, 2003, pp. 50-54, vol. 11.
Wood Thomas F. et al., "Radiofrequency ablation of 231 Unresectable hepatic tumors:indications, limitations, and complications," Ann. Surg. Oncol, 2000, pp. 593-600, vol. 7, Lippincott Williams & Wilkins.
Wu, Xiaohui et al., "A Framework for Calibration of Electromagnetic Surgical Navigation Systems," IEEE RSJ International Conference on Intelligent Robot Systems (IROS), 2003, pp. 547-552, vol. 1, IEEE.
Xu, Sheng et al., "3D Motion Tracking of Pulmonary Lesions Using CT Fluoroscopy Images for Robotically Assisted Lung Biopsy," Proc. SPIE. 5367, Medical Imaging 2004: Visualization, Image-Guided Procedures, and Display, 394. (May 5, 2004), pp. 394-402.
Yamagata, Hitoshi, "Development of a New Display Method for Compound 3D Ultrasound Images: Fusion 3D Images From B-mode and 3D Doppler Images," 1999, pp. 43-46, vol. 70.
Yao, Jianhua et al., "A C-arm fluoroscopy-guided progressive cut refinement strategy using a surgical robot," Computer Aided Surgery, 2000, pp. 373-390, vol. 5—No. 6, Wiley-Liss, Inc.
Yao, Jianhua, et al., "A Progressive Cut Refinement Scheme for Revision Total Hip Replacement Surgery Using C-arm Fluoroscopy," Proceedings of the 2nd International Conference on Medical Image and Computer-Assisted Intervention (MICCAI'99), Springer-Verlag, 1999, pp. 1010-1019, vol. 1679.
Yao, Jianhua et al. "Deformable registration between a statistical born density atlas and X-ray images," Second International Conference on Computer Assisted Orthopaedic Surgery, 2002, pp. 168-169.
Zacherl, Johannes et al., "Current value of intraoperative sonography during surgery for hepatic neoplasms," World J Surg, 2002, pp. 550-554, vol. 26—No. 5.
Zhang, Lunwei et al., "FBG Sensor Devices for Spatial Shape Detection of Intelligent Colonoscope," IEEE International Conference on Robotics and Automation, Apr. 2004, New Orleans, Louisiana, pp. 835-840.
Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.
Zhang, Z., "A Flexible New Technique for Camera Calibration," Technical report MSR-TR-98-71, Microsoft Research, Microsoft Corporation, Redmond, WA, Dec. 1998, pp. 1-21.

\* cited by examiner

MEDICAL ROBOTIC SYSTEM PROVIDING SENSORY FEEDBACK INDICATING A DIFFERENCE BETWEEN A COMMANDED STATE AND A PREFERRED POSE OF AN ARTICULATED INSTRUMENT

CROSS REFERENCE TO RELATED APPLICATIONS

This application is a continuation of application Ser. No. 14/551,283 (filed Nov. 24, 2014), which is a continuation of application Ser. No. 12/704,669 (filed Feb. 12, 2010), now U.S. Pat. No. 8,918,211, each of which is incorporated herein by reference.

FIELD OF THE INVENTION

The present invention generally relates to medical robotic systems and in particular, to a medical robotic system providing sensory feedback indicating a difference between a commanded state and a preferred pose of an articulated instrument.

BACKGROUND

Medical robotic systems such as teleoperative systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

One example of such a medical robotic system is the da Vinci® Surgical System from Intuitive Surgical, Inc., of Sunnyvale, Calif., which is a minimally invasive robotic surgical system. The da Vinci® Surgical System has a number of robotic arms that move attached medical devices, such as an image capturing device and Intuitive Surgical's proprietary EndoWrist® articulating surgical instruments, in response to movement of input devices by a surgeon viewing images captured by the image capturing device of a surgical site. Each of the medical devices is inserted through its own minimally invasive incision into the patient and positioned to perform a medical procedure at the surgical site. The incisions are placed about the patient's body so that the surgical instruments may be used to cooperatively perform the medical procedure and the image capturing device may view it without their robotic arms colliding during the procedure.

To perform certain medical procedures, it may be advantageous to use a single entry aperture, such as a minimally invasive incision or a natural body orifice, to enter a patient to perform a medical procedure. For example, an entry guide may first be inserted, positioned, and held in place in the entry aperture. Articulated instruments such as an articulated camera and a plurality of articulated surgical tools, which are used to perform the medical procedure, may then be inserted into a proximal end of the entry guide so as to extend out of its distal end. Thus, the entry guide accommodates a single entry aperture for multiple instruments while keeping the instruments bundled together as it guides them toward the work site.

A number of challenges arise in medical robotic systems using such a bundled unit, however, because of the close proximity of the articulated camera and tool instruments. For example, because the camera instrument has proximal articulations (e.g., joints) that are not visible from the distal tip camera view, the surgeon can lose track of the current state of such articulations when moving the camera and consequently, their available range of motion. Also, when the articulations of the camera and tool instruments are out of view of the camera and therefore, not visible to the surgeon through its captured images, the surgeon may inadvertently drive links of the tools and/or camera instruments to crash into one another while telerobotically moving the articulated instruments to perform a medical procedure. In either case, the safety of the patient may be jeopardized and the successful and/or timely completion of the medical procedure may be adversely impacted.

OBJECTS AND SUMMARY

Accordingly, one object of one or more aspects of the present invention is a medical robotic system, and method implemented therein, that provides an operator a means for selecting a preferred pose for an articulated instrument, which serves as a biasing point for operator commanded movement of the articulated instrument.

Another object of one or more aspects of the present invention is a medical robotic system, and method implemented therein, that provides a sensory cue to an operator as the operator commands an articulated instrument to be moved from its preferred pose.

Another object of one or more aspects of the present invention is a medical robotic system, and method implemented therein, that provides a haptic force to an operator that nudges the operator to move an articulated instrument back to its preferred pose.

The embodiments of the invention are summarized by the claims that follow below.

Additional objects, features and advantages of the various aspects of the present invention will become apparent from the following description of its preferred embodiment, which description should be taken in conjunction with the accompanying drawings.

DETAILED DESCRIPTION

Figure 1:
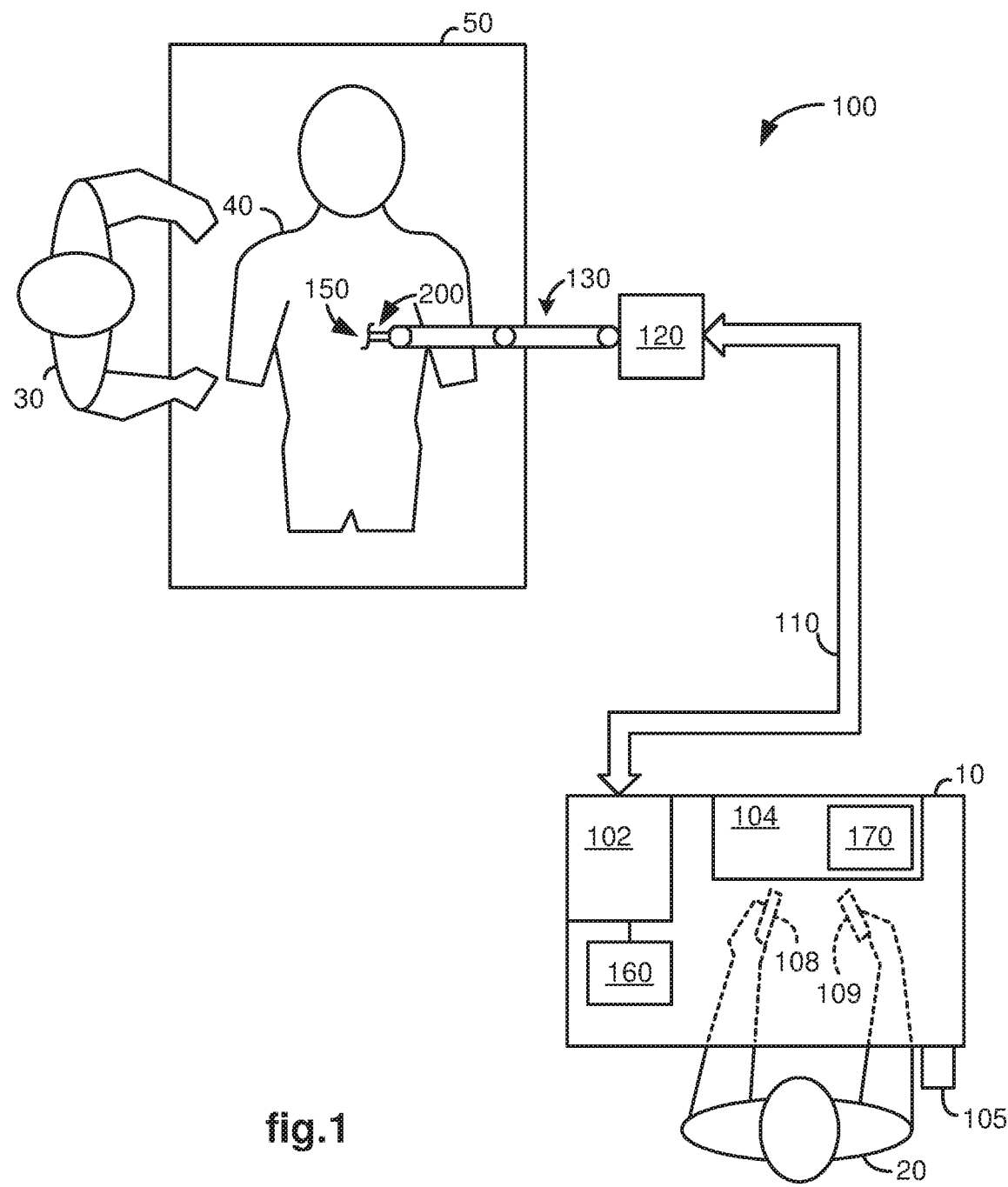
FIG. 1 illustrates a top view of an operating room employing a medical robotic system utilizing aspects of the present invention.

FIG. 1 illustrates, as an example, a top view of an operating room in which a medical robotic system 100 is being utilized by a Surgeon 20 for performing a medical procedure on a Patient 40 who is lying face up on an operating table 50. One or more Assistants 30 may be positioned near the Patient 40 to assist in the procedure while the Surgeon 20 performs the procedure teleoperatively by manipulating input devices 108, 109 on a surgeon console 10.

In the present example, an entry guide (EG) 200 is inserted through a single entry aperture 150 into the Patient 40. Although the entry aperture 150 is a minimally invasive incision in the present example, in the performance of other medical procedures, it may instead be a natural body orifice. The entry guide 200 is held and manipulated by a robotic arm assembly 130.

As with other parts of the medical robotic system 100, the illustration of the robotic arm assembly 130 is simplified in FIG. 1. In one example of the medical robotic system 100, the robotic arm assembly 130 includes a setup arm and an entry guide manipulator. The setup arm is used to position the entry guide 200 at the entry aperture 150 so that it properly enters the entry aperture 150. The entry guide manipulator is then used to robotically insert and retract the entry guide 200 into and out of the entry aperture 150. It may also be used to robotically pivot the entry guide 200 in pitch, roll and yaw relative to a longitudinal axis of the entry guide 200 about a pivot point (also referred to as a remote center "RC") which is located at the entry aperture 150.

The console 10 includes a three-dimensional (3-D) monitor 104 for displaying a 3-D image of a surgical site to the Surgeon, left and right hand-manipulatable input devices 108, 109, a foot pedal 105, and a processor 102. The input devices 108, 109 may include any one or more of a variety of input devices such as joysticks, gloves, trigger-guns, hand-operated controllers, or the like. Other input devices that are provided to allow the Surgeon to interact with the medical robotic system 100 include a foot pedal 105, a conventional voice recognition system 160, a Graphical User Interface (GUI) 170, and convention computer inputs such as a keyboard and computer mouse.

The console 10 is usually located in the same room as the Patient so that the Surgeon may directly monitor the procedure, is physically available if necessary, and is able to speak to the Assistant(s) directly rather than over the telephone or other communication medium. However, the Surgeon can also be located in a different room, a completely different building, or other remote location from the Patient allowing for remote surgical procedures.

Figure 3:
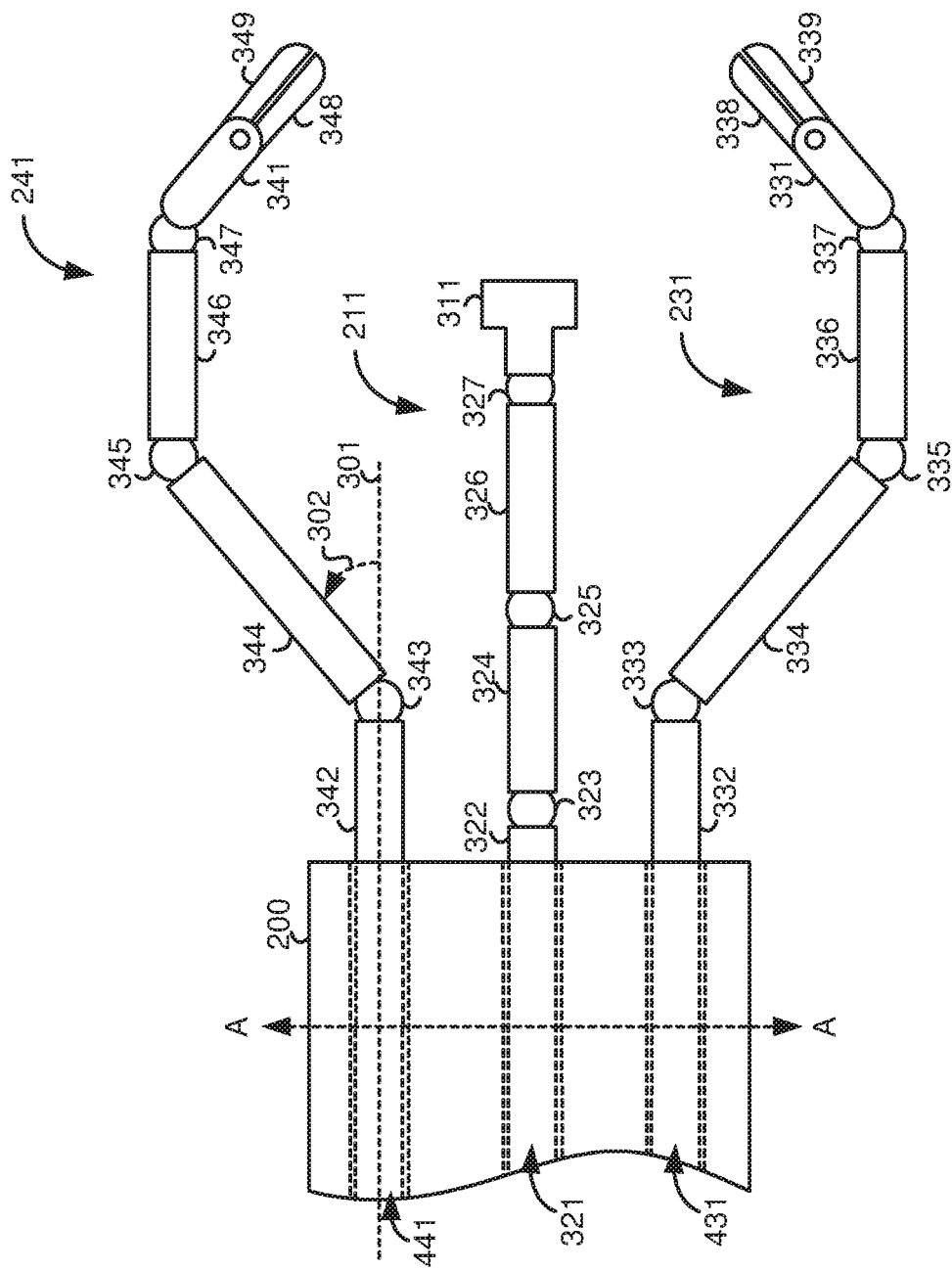
FIGS. 3-4 respectively illustrate top and right side views of articulated instruments extending out of a distal end of an entry guide in a medical robotic system utilizing aspects of the present invention.
Figure 4:
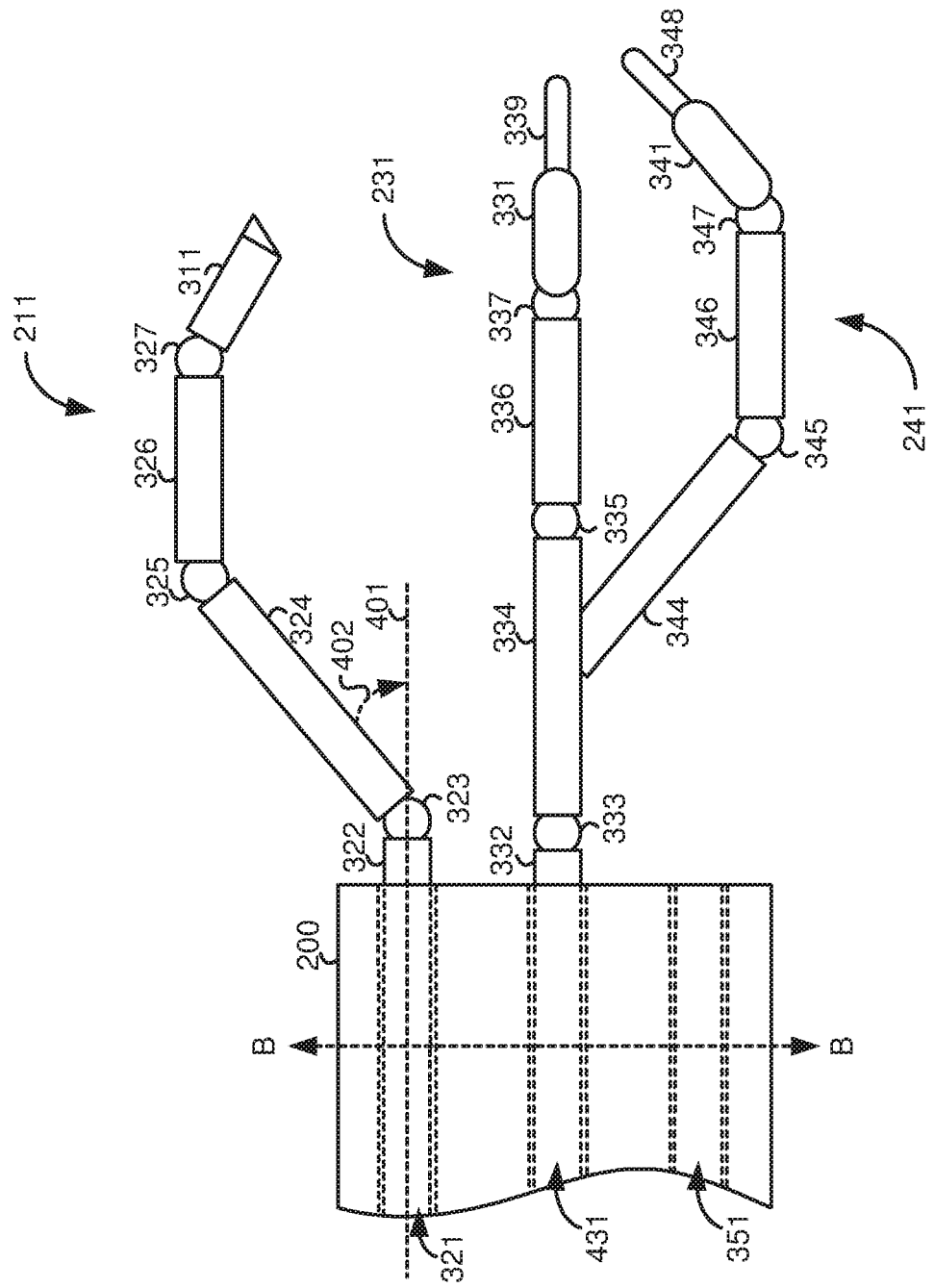
Figure 5:
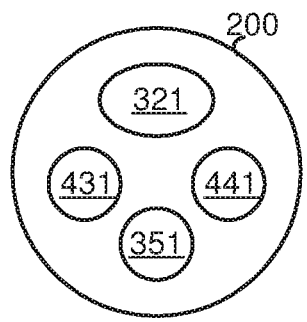
FIG. 5 illustrates a distal end view of an entry guide with passages defined therein as used in a medical robotic system utilizing aspects of the present invention.

As shown in FIGS. 3-4, the entry guide 200 has articulated instruments such as surgical tools 231, 241 and a stereo camera 211 extending out of its distal end. Although only two tools 231, 241 are shown, the entry guide 200 may guide additional instruments as required for performing a medical procedure at a work site in the Patient. For example, as shown in the entry guide 200 side and distal end views of FIGS. 4 and 5, passage 351 is available for extending another articulated instrument through the entry guide 200 and out through its distal end. Each of the surgical tools 231, 241 is associated with one of the input devices 108, 109 in a tool following mode. The Surgeon performs a medical procedure by manipulating the input devices 108, 109 so that the processor 102 causes corresponding movement of their respectively associated surgical tools 231, 241 while the Surgeon views the work site in 3-D on the console monitor 104 as images of the work site are being captured by the camera 211.

In this example, input devices 108, 109 will be provided with at least the same degrees of freedom as their associated tools 231, 241 to provide the Surgeon with telepresence, or the perception that the input devices 108, 109 are integral with the tools 231, 241 so that the Surgeon has a strong sense of directly controlling the tools 231, 241. To this end, the monitor 104 is also positioned near the Surgeon's hands so that it will display a projected image that is oriented so that the Surgeon feels that he or she is actually looking directly down onto the work site and images of the tools 231, 241 appear to be located substantially where the Surgeon's hands are located.

In addition, the real-time image on the monitor 104 is projected into a perspective image such that the Surgeon can manipulate the end effectors 331, 341 of the tools 231, 241 through their corresponding input devices 108, 109 as if viewing the work site in substantially true presence. By true presence, it is meant that the presentation of an image is a true perspective image simulating the viewpoint of an operator that is physically manipulating the end effectors 331, 341. Thus, the processor 102 may transform the coordinates of the end effectors 331, 341 to a perceived position so that the perspective image being shown on the monitor 104 is the image that the Surgeon would see if the Surgeon was located directly behind the end effectors 331, 341.

The processor 102 performs various functions in the system 100. One important function that it performs is to implement the various controllers described herein to translate and transfer the mechanical motion of input devices 108, 109 through control signals over bus 110 so that the Surgeon can effectively manipulate and otherwise move devices, such as the tools 231, 241, camera 211, and entry guide 200, that are selectively associated with the input devices 108, 109 at the time.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system.

For additional details on the construction and operation of general aspects of a medical robotic system such as described herein, see, e.g., U.S. Pat. No. 6,493,608 "Aspects of a Control System of a Minimally Invasive Surgical Apparatus," U.S. Pat. No. 6,671,581 "Camera Referenced Control in a Minimally Invasive Surgical Apparatus," and U.S. Pat. Application Pub. No. U.S. 2008/007129 "Minimally Invasive Surgical System," which are incorporated herein by reference.

Figure 2:
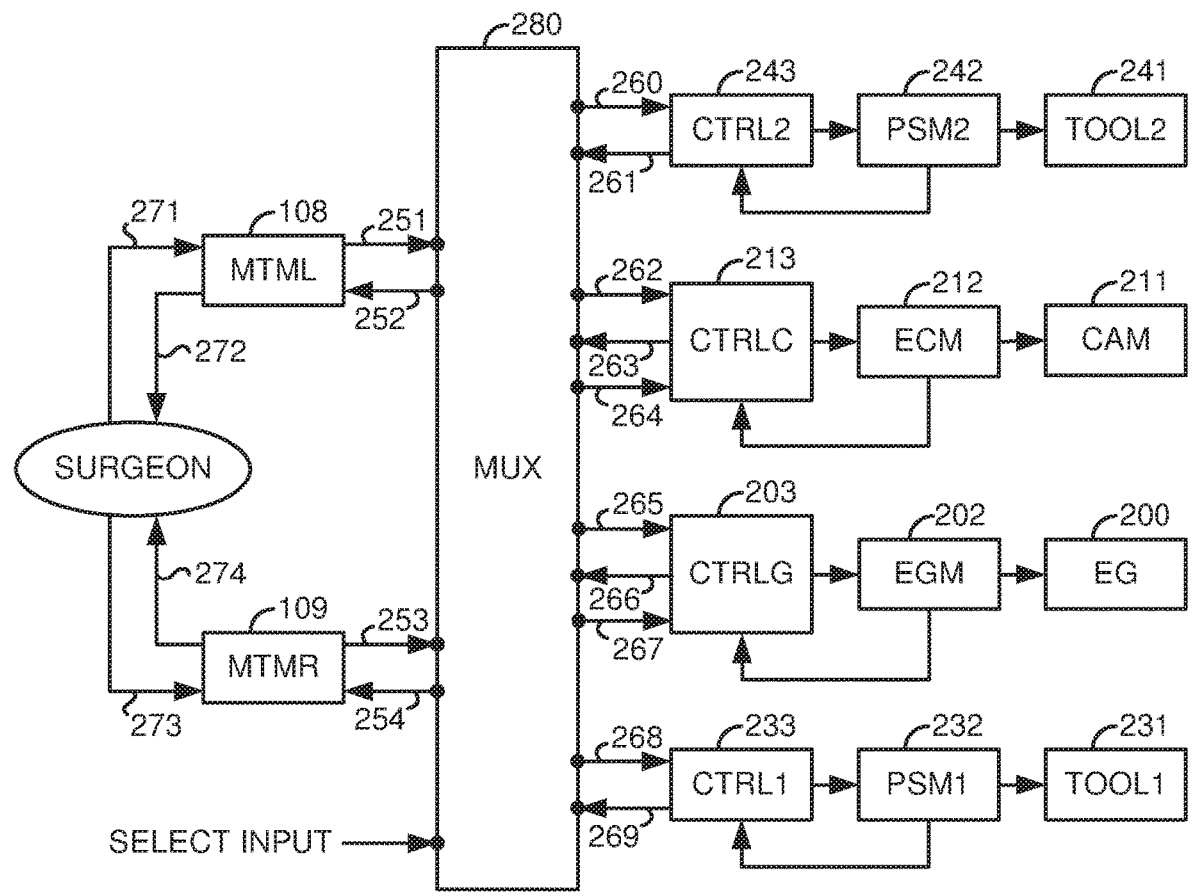
FIG. 2 illustrates a block diagram of components for controlling and selectively associating device manipulators to left and right hand-manipulatable input devices in a medical robotic system utilizing aspects of the present invention.

FIG. 2 illustrates, as an example, a block diagram of components for controlling and selectively associating device manipulators (and their respective devices) to the input devices 108, 109. Various surgical tools such as graspers, cutters, and needles may be used to perform a medical procedure at a work site within the Patient. In this example, two surgical tools 231, 241 are used to robotically perform the procedure and the camera 211 is used to view the procedure. The tools 231, 241 and camera 211 are inserted through passages in the entry guide 200. As described in reference to FIG. 1, the entry guide 200 is inserted into the Patient through entry aperture 150 using the setup portion of the robotic arm assembly 130 and maneuvered by the entry guide manipulator (EGM) 202 of the robotic arm assembly 130 towards the work site where the medical procedure is to be performed.

Each of the devices 231, 241, 211, 200 is manipulated by its own manipulator. In particular, the camera 211 is manipulated by a camera manipulator (ECM) 212, the first surgical tool 231 is manipulated by a first tool manipulator (PSM1) 232, the second surgical tool 241 is manipulated by a second tool manipulator (PSM2) 242, and the entry guide 200 is manipulated by an entry guide manipulator (EGM) 202.

Each of the instrument manipulators 232, 242, 212 is a mechanical assembly that carries actuators and provides a mechanical, sterile interface to transmit motion to its respective articulated instrument. Each instrument 231, 241, 211 is a mechanical assembly that receives the motion from its manipulator and, by means of a cable transmission, propagates it to the distal articulations (e.g., joints). Such joints may be prismatic (e.g., linear motion) or rotational (e.g., they pivot about a mechanical axis). Furthermore, the instrument may have internal mechanical constraints (e.g., cables, gearing, cams and belts, etc.) that force multiple joints to move together in a pre-determined fashion. Each set of mechanically constrained joints implements a specific axis of motion, and constraints may be devised to pair rotational joints (e.g., joggle joints). Note also that in this way the instrument may have more joints than the available actuators.

Since the controllers 233, 243, 213 are generally implemented as computer code in the processor 102, they are each programmed to be reconfigurable by an operator of the system 100 to control either a tool or a camera instrument. Thus, if a tool instrument is physically switched for a camera instrument or vice versa in the system, its controller may be reconfigured to accommodate the newly installed device.

In this example, each of the input devices 108, 109 may be selectively associated with one of the devices 211, 231, 241, 200 so that the associated device may be controlled by the input device through its controller and manipulator. The operator may perform such selection in a conventional manner by interacting with a menu on the GUI 170 or providing voice commands recognized by the voice recognition system 160 or by inputting such associations into the system 100 using an input device such as a touchpad (not shown) or interacting with special purpose buttons provided on the input devices 108, 109 or foot pedal 105. In each such implementation, a select input is generated and provided to a multiplexer (MUX) 280, which is also generally implemented in the processor 102. Depending upon the value (i.e., the combination of 1's and 0's) provided by the select input, different combinations of cross-switching are selectable.

For example, a first value for the select input to the MUX 280 places the left and right input devices 108, 109 in "tool following modes" wherein they are respectively associated with the first and second surgical tools 241, 231, which are telerobotically controlled through their respective controllers 243, 233 and manipulators 242, 232 so that the Surgeon may perform a medical procedure on the Patient while the entry guide 200 is locked in place. In this configuration, the MUX 280 cross-switches to respectively connect output and input 251, 252 of the input device 108 to input and output 260, 261 of the tool controller 243; and respectively connect output and input 253, 254 of the input device 109 to input and output 268, 269 of the tool controller 233.

When the camera 211 or the entry guide 200 is to be repositioned by the Surgeon, either one or both of the left and right input devices 108, 109 may be associated with the camera 211 or entry guide 200 so that the Surgeon may move the camera 211 or entry guide 200 through its respective controller (213 or 203) and manipulator (212 or 202). In this case, the disassociated one(s) of the surgical tools 231, 241 is locked in place relative to the entry guide 200 by its controller.

For example, a second value for the select input to the MUX 280 places the left and right input devices 108, 109 in a "two-handed, camera positioning mode" wherein they are associated with the camera 211, which is telerobotically controlled through its controller 213 and manipulator 212 so that the Surgeon may position the camera 211 while the surgical tools 231, 241 and entry guide 200 are locked in place by their respective controllers 233, 243, 203. In this case, the input devices 108, 109 may be used in tandem to control the camera instrument 211, such as using a virtual handlebar image referenced control technique in which a point midway between pivot points of the input devices 108, 109 is used to control movement of the camera instrument 211. In this configuration, the MUX 280 cross-switches to respectively connect output and input 251, 252 of the input device 108 to input and output 262, 263 of the camera controller 213; and respectively connect output and input 253, 254 of the input device 109 to input and output 264, 263 of the camera controller 213.

On the other hand, a third value for the select input to the MUX 280 places the left and right input devices 108, 109 in an "two-handed, entry guide positioning mode" wherein they are associated with the entry guide 200, which is telerobotically controlled through its controller 203 and manipulator 202 so that the Surgeon may position the entry guide 200 while the surgical tools 231, 241 and camera 211 are locked in place relative to the entry guide 200 by their respective controllers 233, 243, 213. In this configuration, the MUX 280 cross-switches to respectively connect output and input 251, 252 of the input device 108 to input and output 262, 263 of the camera controller 213; and respectively connect output and input 253, 254 of the input device 109 to input and output 264, 263 of the camera controller 213.

If only one of the input devices 108, 109 is to be used for positioning the camera 211 or the entry guide 200, then another value for the select input to the MUX 280 may be provided by the operator to place the selected input device in a "single-handed, camera or entry guide positioning mode" so that the selected input device is associated with the camera or entry guide, as the case may be, which is telerobotically controlled through its controller and manipulator so that the Surgeon may position the device. Meanwhile, the other input device may either be "soft locked" in position by its controller until the camera or entry guide positioning is completed or the other input device may still be available to the Surgeon to control its associated surgical tool during camera or entry guide repositioning. For example, when the input device 108 is in "single-handed, camera positioning mode," the MUX 280 cross-switches to respectively connect output and input 251, 252 of the input device 108 to input and output 262, 263 of the camera controller 213. In this case, no connection is made to the second input 264 of the camera controller 213.

FIGS. 3-4 respectively illustrate, as examples, top and right side views of a distal end of the entry guide 200 with the camera 211 and surgical tools 231, 241 extending outward. The articulated camera 211 extends through passage 321 and the articulated surgical tools 231, 241 respectively extend through passages 431, 441 of the entry guide 200. The camera 211 includes a tip 311, first, second, and third links 322, 324, 326, first and second joint assemblies (also referred to herein simply as "joints") 323, 325, and a wrist assembly 327. The tip 311 houses a stereo camera connected to a camera controller and a fiber-optic cable connected to an external light source. The first joint assembly 323 couples the first and second links 322, 324 and the second joint assembly 325 couples the second and third links 324, 326 so that the second link 324 may pivot about the first joint assembly 323 in pitch and yaw while the first and third links 322, 326 remain parallel to each other.

The first and second joints 323, 325 are referred to as "joggle joints", because they cooperatively operate together so that as the second link 324 pivots about the first joint 323 in pitch and/or yaw, the third link 326 pivots about the second joint 325 in a complementary fashion so that the first and third links 322, 326 always remain parallel to each other. The first link 322 may also rotate around its longitudinal axis in roll as well as move in and out (e.g., insertion towards the work site and retraction from the worksite) through the passage 321. The wrist assembly 327 also has pitch and yaw angular movement capability so that the camera's tip 311 may be oriented up or down and to the right or left, and combinations thereof.

The joints and links of the tools 231, 241 are similar in construction and operation to those of the camera 211. In particular, the tool 231 includes an end effector 331 (having jaws 338, 339), first, second, and third links 332, 334, 336, first and second joint assemblies 333, 335, and a wrist assembly 337 that are driven by actuators such as described in reference to FIG. 6 (plus an additional actuator for actuating the end effector 331). Likewise, the tool 241 includes an end effector 341 (having jaws 348, 349), first, second, and third links 342, 344, 346, first and second joint assemblies 343, 345, and a wrist assembly 347 that are also driven by actuators such as described in reference to FIG. 6 (plus an additional actuator for actuating the end effector 341).

Figure 6:
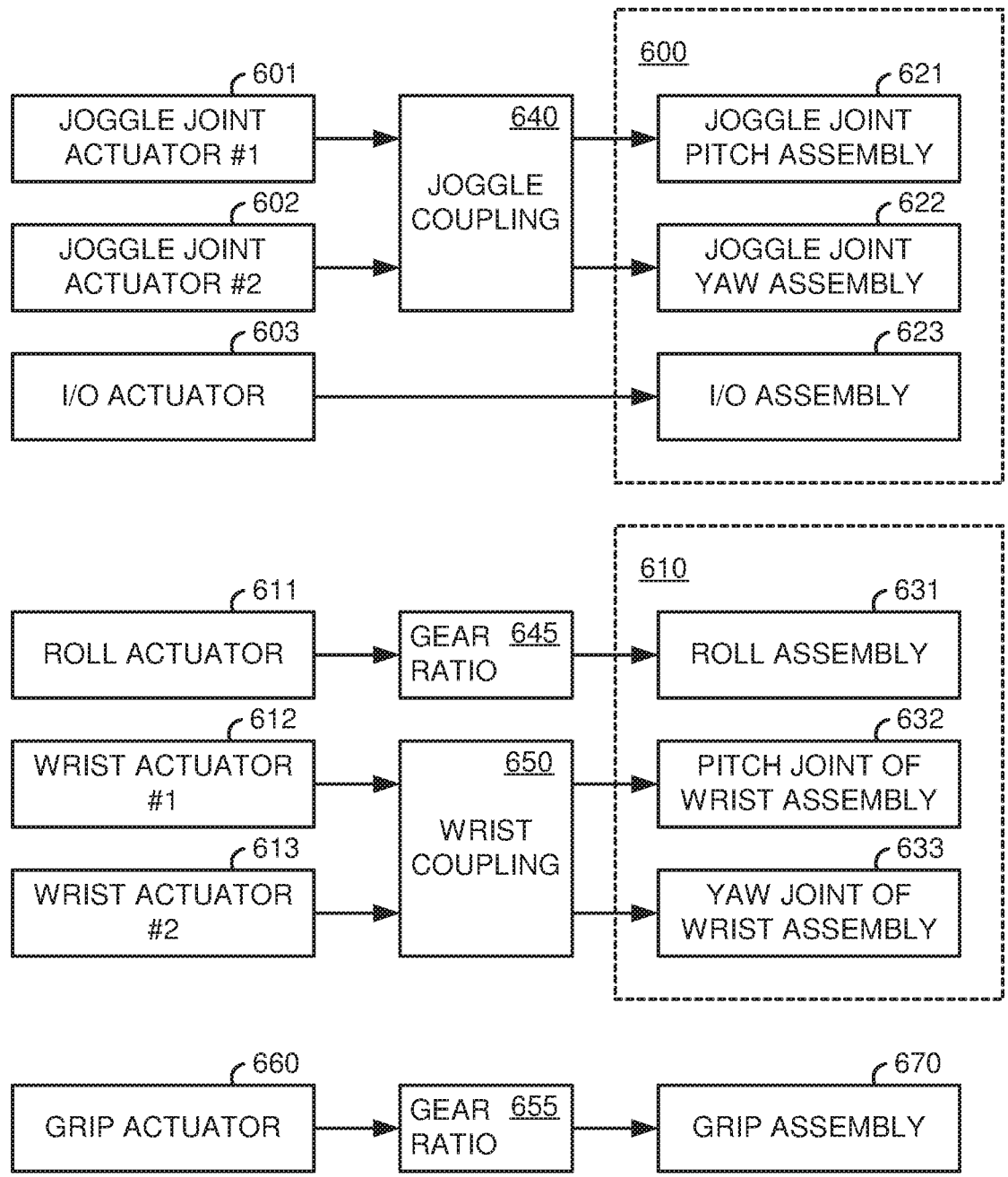
FIG. 6 illustrates a block diagram of interacting components of an articulated instrument manipulator and an articulated instrument as used in a medical robotic system utilizing aspects of the present invention.

FIG. 6 illustrates, as an example, a diagram of interacting parts of an articulated instrument (such as the articulated camera 211 and the articulated surgical tools 231, 241) and its corresponding instrument manipulator (such as the camera manipulator 212 and the tool manipulators 232, 242). Each of the instruments includes a number of actuatable assemblies 621-623, 631-633, 670 for effectuating movement of the instrument (including its end effector), and its corresponding manipulator includes a number of actuators 601-603, 611-613, 660 for actuating the actuatable assemblies.

In addition, a number of interface mechanisms may also be provided. For example, pitch/yaw coupling mechanisms 640, 650 (respectively for the joggle joint pitch/yaw and the wrist pitch/yaw) and gear ratios 645, 655 (respectively for the instrument roll and the end effector actuation) are provided in a sterile manipulator/instrument interface to achieve the required range of motion of the instrument joints in instrument joint space while both satisfying compactness constraints in the manipulator actuator space and preserving accurate transmissions of motion across the interface. Although shown as a single block 640, the coupling between the joggle joint actuators 601, 602 (differentiated as #1 and #2) and joggle joint pitch/yaw assemblies 621, 622 may include a pair of coupling mechanisms—one on each side of the sterile interface (i.e., one on the manipulator side of the interface and one on the instrument side of the interface). Likewise, although shown as a single block 650, the coupling between the wrist actuators 612, 613 (differentiated as #1 and #2) and wrist pitch/yaw joint assemblies 632, 633 may also comprise a pair of coupling mechanisms—one on each side of the sterile interface.

Both the joggle joint pitch assembly 621 and the joggle joint yaw assembly 622 share the first, second and third links (e.g., links 322, 324, 326 of the articulated camera 211) and the first and second joints (e.g., joints 322, 325 of the articulated camera 211). In addition to these shared components, the joggle joint pitch and yaw assemblies 621, 622 also include mechanical couplings that couple the first and second joints (through joggle coupling 640) to the joggle joint pitch and yaw actuators 601, 602 so that the second link may controllably pivot about a line passing through the first joint and along an axis that is latitudinal to the longitudinal axis of the first link (e.g., link 322 of the articulated camera 211) and the second link may controllably pivot about a line passing through the first joint and along an axis that is orthogonal to both the latitudinal and longitudinal axes of the first link.

The in/out (I/O) assembly 623 includes the first link (e.g., link 322 of the articulated camera 211) and interfaces through a drive train coupling the in/out (I/O) actuator 603 to the first link so that the first link is controllably moved linearly along its longitudinal axis 401 by actuation of the I/O actuator 603. The roll assembly 631 includes the first link and interfaces through one or more gears (i.e., having the gear ratio 645) that couple a rotating element of the roll actuator 611 (such as a rotor of a motor) to the first link so that the first link is controllably rotated about its longitudinal axis by actuation of the roll actuator 611.

The instrument manipulator (e.g., camera manipulator 212) includes wrist actuators 612, 613 that actuate through wrist coupling 650 pitch and yaw joints 632, 633 of the wrist assembly (e.g., wrist assembly 327 of the articulated camera 211) so as to cause the instrument tip (e.g., camera tip 311) to controllably pivot in an up-down (i.e., pitch) and side-to-side (i.e., yaw) directions relative to the wrist assembly. The grip assembly 670 includes the end effector (e.g., end effector 331 of the surgical tool 231) and interfaces through one or more gears (i.e., having the gear ratio 655) that couple the grip actuator 660 to the end effector so as to controllably actuate the end effector.

Figure 7:
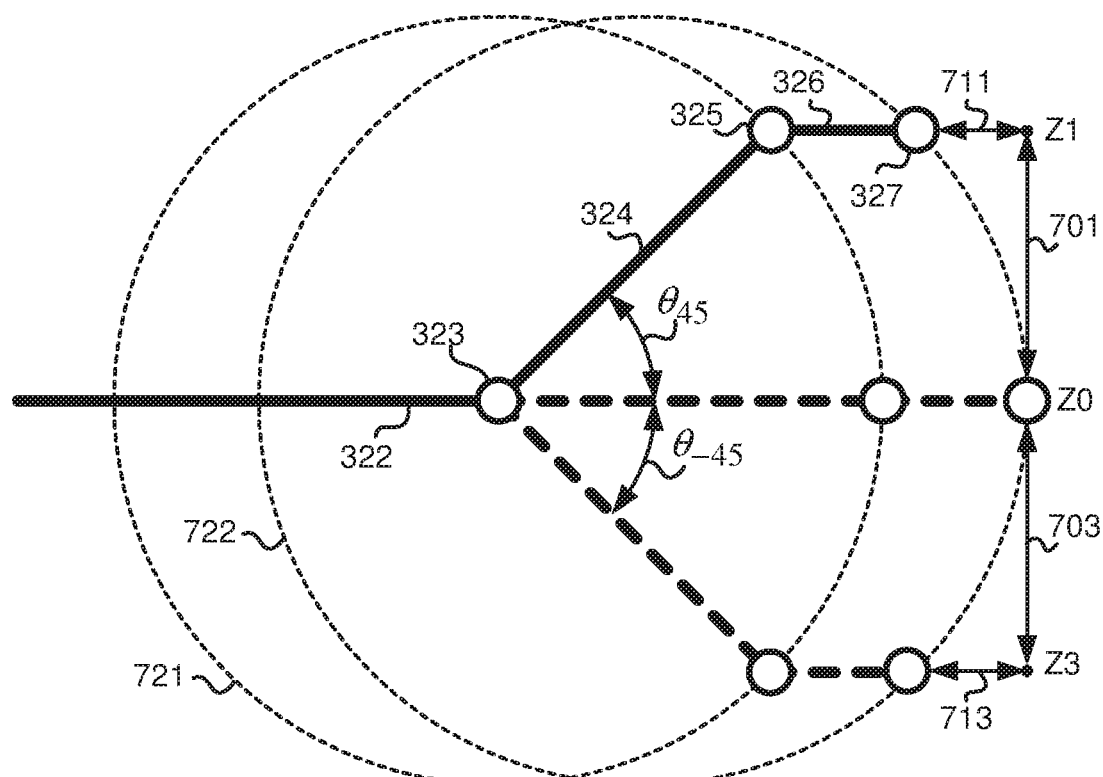
FIG. 7 illustrates a schematic kinematic diagram including a camera joggle-joint pitch assembly with indications of arc compensation for translating its movement to a translational mode movement, as used in a medical robotic system utilizing aspects of the present invention.

The group of instrument joints 600 is referred to as "translational joints" because by actuation of a combination of these joints, the instrument's wrist assembly may be positioned translationally within three-dimensional space. For example, FIG. 7 illustrates a schematic kinematic diagram of the links 322, 324, 326 and joints 323, 325 of the joggle joint pitch assembly 621 of the articulated camera 211 at three pitch angles, $\theta=+45$, $\theta=0$, $\theta=-45$ degrees, with indications of corresponding arc compensation by the in/out assembly 623 so as to result in translational movement of the wrist assembly 327 in a first direction (vertical in the figure) which is orthogonal to the longitudinal axis (horizontal in the figure) of the first link 322. An indication of the longitudinal axis 401 of the first link 322 and the pitch angle 402 are shown in FIG. 4. If the camera tip 311 is in a fixed orientation relative to the wrist assembly 327 during the translational movement, then the camera tip 311 will also move in an arc corresponding to that of the wrist assembly 327 offset by a fixed length dependent upon the angle of orientation.

In this example, when the links 322, 324, 326 are fully extended outward so that the pitch angle is 0 degrees and the wrist assembly 327 is at a point Z0, no arc compensation is necessary by the in/out assembly 623 if the wrist assembly 327 is to be moved in a vertical direction along a line passing through the point Z0. On the other hand, when the second link 324 is rotated +45 degrees in pitch at the first joint 323 about a first axis which is orthogonal to the longitudinal axis 401 of the link 322, the position of the wrist assembly 327 relative to the first joint 323 has a tangential component 701. In order for the movement of the wrist assembly 327 to move in the vertical direction along the line passing through the point Z0, however, the in/out assembly 623 must move the wrist assembly 327 forward (i.e., in) to the point Z1 by a distance indicated as 711. Similarly, if the second link 324 is rotated −45 degrees in pitch at the first joint 323 about the first axis, the position of the wrist assembly 327 relative to the first joint 323 has a tangential component 703 and the in/out assembly 623 must move the wrist assembly 327 forward to a point Z3 by a distance indicated as 713 in order for the movement of the wrist assembly 327 to move along the vertical line passing through the point Z0. For other angles of pitch rotation, the second joint 325 moves along a circle 721 having a radius equal to the length of the second link 324, the wrist assembly 327 moves along a corresponding circle 722 of equal radius that is offset from the circle 721 by an amount equal to the length of the third link 326 along the longitudinal axis of the first link 322, and the arc compensation required by the in/out assembly 623 is the distance from the wrist assembly 327 to the vertical line passing through the point Z0.

The joggle joint yaw assembly 622 operates in a similar manner as the joggle joint pitch assembly 621. Except that in this case, the second link 324 is rotated at the first joint 323 about a second axis which is orthogonal to both the first axis (as used by the pitch assembly 621) and the longitudinal axis 401 of the link 322.

When the joggle joint pitch and yaw assemblies 621, 622 are actuated concurrently, such as through joggle coupling 640, the resulting movement of the wrist assembly 327 may follow a portion of a sphere (i.e., a three-dimensional version of the circle 722). In this case, if the movement of the wrist assembly 327 is to be on a plane passing through and perpendicular to the longitudinal axis of the link 322, then the compensation required by the in/out assembly 623 is the distance from the wrist assembly 327 to the plane.

Note that in the above example, it is assumed that both the joggle joint pitch and yaw assemblies 621, 622 pivot the second link 324 about the same pivot point. In practice, however, they may pivot about slightly different pivot points if the first and second joints 323, 325 are first and second joint assemblies in which each joint assembly includes a pitch joint, a yaw joint and a short link separating and coupling the pitch and yaw joints. In this case, first and second pitch joints respectively of the first and second joint assemblies 323, 325 are coupled together as part of the joggle joint pitch assembly 621, and first and second yaw joints respectively of the first and second joint assemblies 323, 325 are coupled together as part of the joggle joint yaw assembly 622. First and second short links of the first and second joint assemblies 323, 325 are referred to as being short, because they are each shorter than the first link 322, second link 324 and third link 326. The first and second short links are also constrained to be parallel to each other at all times, like the first and third links 322, 326. In addition, as may be readily appreciated in light of the geometries of the first and second joint assemblies 323, 325, rather than moving along the surface of a sphere, the wrist assembly 327 may follow a different concave virtual surface when both the joggle joint pitch and yaw assemblies 621, 622 are actuated at the same time.

Figure 8:
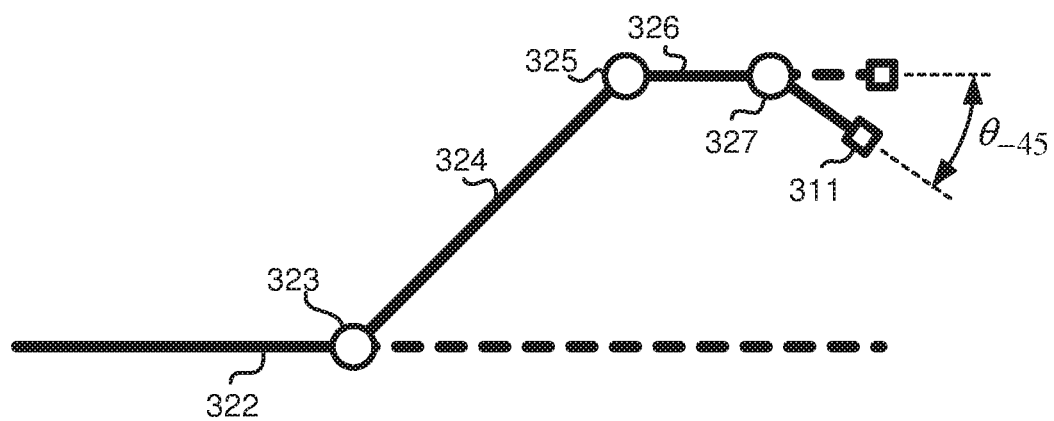
FIG. 8 illustrates a schematic kinematic diagram including a camera wrist assembly for providing orientational mode movement, as used in a medical robotic system utilizing aspects of the present invention.

The group of instrument joints 610 is referred to as "orientational joints" because by actuation of these joints, the instrument's tip may be oriented about the wrist assembly. For example, FIG. 8 illustrates a schematic kinematic diagram including the wrist assembly 327 as it pivots the camera's tip 311 about its pitch joint 632 to a −45 degrees pitch angle while the links 322, 324, 326 and joints 323, 325 of the camera instrument's joggle-joint pitch assembly 621 are controllably held in place. The wrist assembly 327 may also pivot the camera's tip 311 about its yaw joint 633 in a similar manner. When the camera's tip 311 is pivoted about both the pitch and yaw joints 632, 633 concurrently by operation of the wrist assembly 327, such as through wrist coupling 650, the resulting movement of the camera tip 311 may follow a concave virtual surface. However, if the pitch and yaw joints 632, 633 are the same joint, such as a ball joint, then the resulting movement of the camera tip 311 may follow a portion of a sphere.

Figure 9:
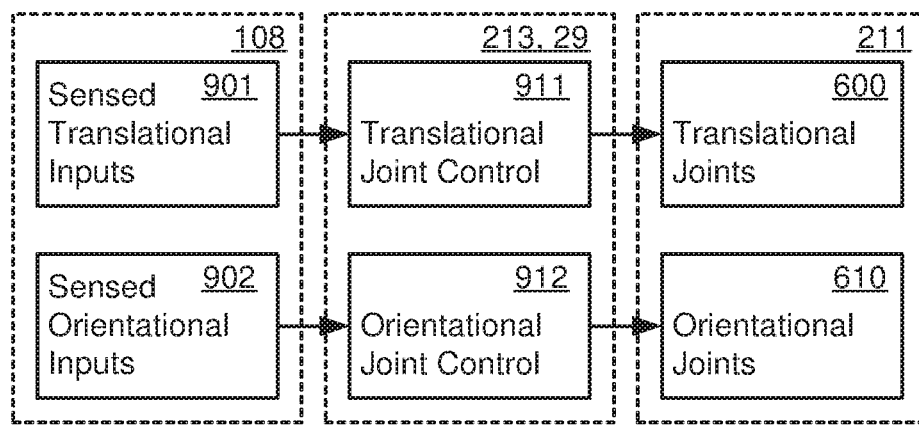
FIG. 9 illustrates a block diagram of a camera instrument control scheme using a single input device for concurrent translational and orientational mode control, as used in a medical robotic system utilizing aspects of the present invention.

FIG. 9 illustrates a block diagram in which the input device 108 is associated with and used to control positioning (i.e., translationally and orientationally) of the tip 311 of the camera instrument 211. In this example, operator manipulated movement of the three translational degrees-of-freedom of the input device 108 is sensed and used to command translational movement of the camera's wrist assembly 327 through translational joints 600 of the camera instrument 211, and operator manipulated movement of the three orientational degrees-of-freedom of the input device 108 is sensed and used to command orientational movement of the camera's tip 311 about its wrist assembly 327 through orientational joints 610 of the camera instrument 211. Because of this partitioning of the translational and orientational modes, the Surgeon generally knows which joints of the camera instrument 211 are moving (i.e., the translational joints 600 or the orientational joints 610) when manipulating the input device 108, thus providing an intuitive sense to the operator of the likelihood that the links of the camera instrument 211 will collide with the links of one of the surgical tools 231, 241 during the camera positioning process.

Figure 10:
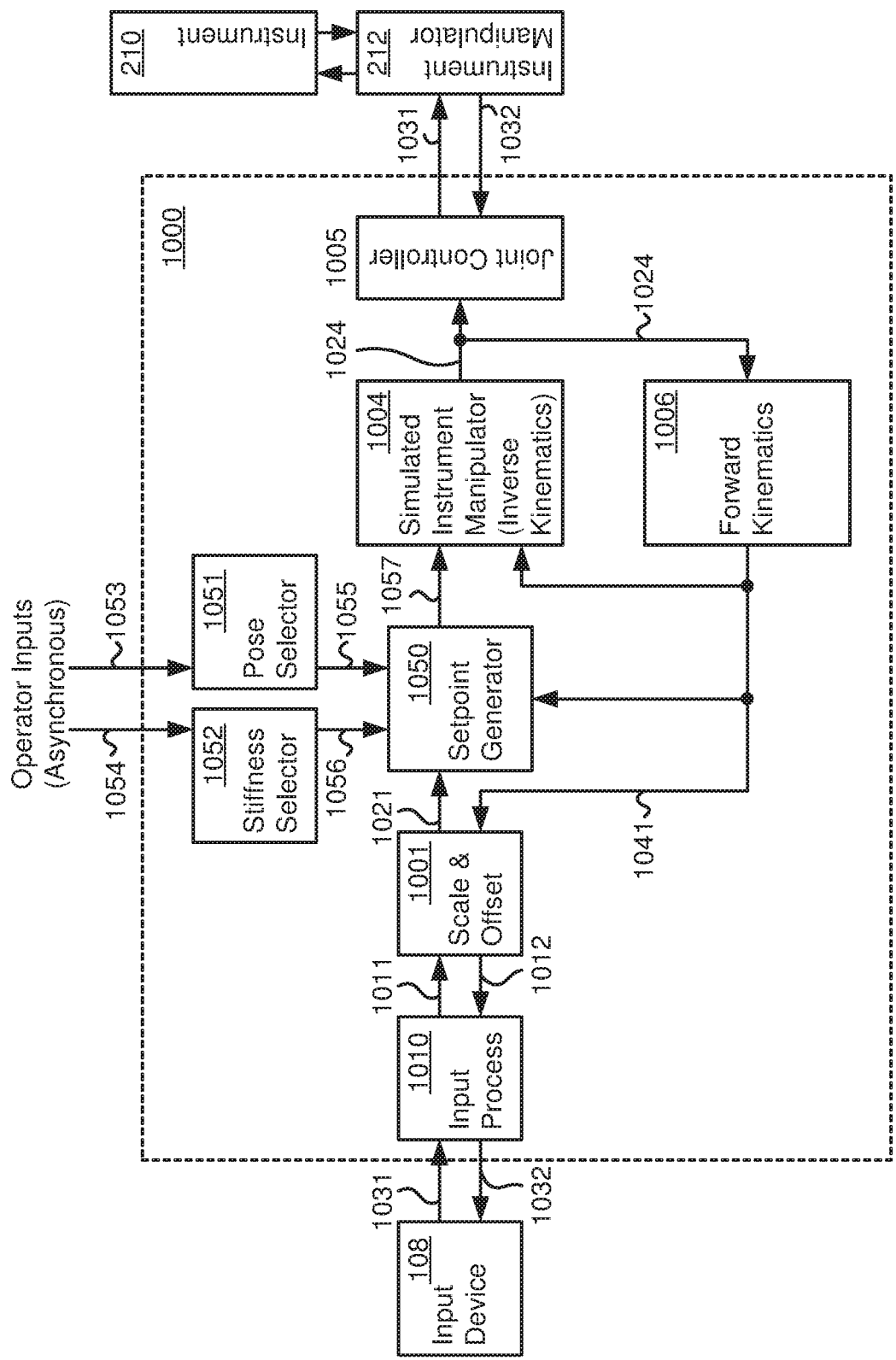
FIG. 10 illustrates a block diagram of a control system for controlling movement of an articulated camera instrument in a medical robotic system utilizing aspects of the present invention.

FIG. 10 illustrates, as an example, a block diagram of a control system 1000 for controlling positioning (i.e., both translationally and orientationally) of the camera instrument 211 in response to movement of the input device 108 when the input device 108 is selectively associated with the camera 211. Although control of the camera 211 is described, it is to be appreciated that the various blocks described herein for the control system 1000 are also applicable to the control of each of the tools 231, 241 as well as the entry guide 200. The input device 108 includes a number of links connected by joints so as to facilitate multiple degrees-of-freedom movement. For example, as the Surgeon/operator moves the input device 108 from one position to another, sensors associated with the joints of the input device 108 sense such movement at sampling intervals (appropriate for the processing speed of the processor 102 and camera control purposes) and provide digital information 1031 indicating such sampled movement in joint space to input processing blocks 1010.

Input processing block 1010 processes the information 1031 received from the joint sensors of the input device 108 to transform the information into corresponding desired positions and velocities for the camera 211 in its Cartesian space relative to a reference frame associated with the position of the Surgeon's eyes (the "eye reference frame"), by computing joint velocities from the joint position information and performing the transformation using a Jacobian matrix and eye related information using well-known transformation techniques.

Scale and offset processing block 1001 receives the processed information 1011 from the input processing block 1010 and applies scale and offset adjustments to the information so that the resulting movement of the camera instrument 211 and consequently, the image being viewed on the monitor 104 appears natural and as expected by the operator of the input device 108. The scale adjustment is useful where small movements of the camera 211 are desired relative to larger movement of the input device 108 in order to allow more precise movement of the camera instrument 211 as it views the work site. In addition, offset adjustments are applied for aligning the input device 108 with respect to the Surgeon's eyes as he or she manipulates the input device 108 to command movement of the camera instrument 211 and consequently, its captured image that is being displayed at the time on the monitor 104.

A setpoint generator block 1050 receives the commanded state vector ($\hat{X}_{DES}$) for the camera instrument 211 in the output 1021 of the scale and offset processing block 1001, a preferred pose vector ($\hat{X}_{PP}$) for the camera instrument 211 in an output 1055 of a pose selector block 1051, and weightings ($w_i$, i=1 . . . n) for the state variables of the commanded state vector ($\hat{X}_{DES}$)' and calculates a setpoint vector ($\hat{X}_{SP}$) for its output 1057 by interpolating between the commanded state vector ($\hat{X}_{DES}$) and the preferred pose vector ($\hat{X}_{PP}$) using the weightings ($w_i$, i=1 . . . n) in a weighted average approach.

For example, the set point value "$f(\hat{X}_{SP_i})$" for the $i^{th}$ state variable of the setpoint vector ($\hat{X}_{SP}$) may be calculated according to the following equation:

$$f(\hat{X}_{SP_i}) = (1-w_i)^* f(\hat{X}_{DES_i}) + w_i^* f(\hat{X}_{PP_i}), \text{ for } 0 < w_i < 1 \quad (1)$$

where "i" indicates the $i^{th}$ state variable, "$w_i$" is a weighting for the $i^{th}$ state variable, "$f(\hat{X}_{DES_i})$" is the value for the $i^{th}$ state variable of the commanded state vector ($\hat{X}_{DES}$) for the camera instrument 211, and "$f(\hat{X}_{PP_i})$" is the value for the $i^{th}$ state variable of the preferred pose vector ($\hat{X}_{PP}$) for the camera instrument 211.

State variables for the commanded state vector ($\hat{X}_{SP}$), the preferred pose vector ($\hat{X}_{PP}$), and the setpoint vector ($\hat{X}_{SP}$) preferably include translational and orientational positions and velocities for six degrees of freedom movement. Weighting coefficients can be individually selected so as to provide stiffer behavior along a specific Cartesian direction for translational movements and/or about a specified Cartesian for rotational movements. Although weightings are used for both positions and velocities of the commanded state vector ($\hat{X}_{DES}$), they are not necessarily independent of each other. In particular, the weightings for velocities may be selected, or otherwise determined in some fashion, so as to be consistent with the weightings of their respective positions (e.g., weightings for corresponding positions and velocities may be either both relatively large or both relatively small, but not one large with the other small).

Figure 11:
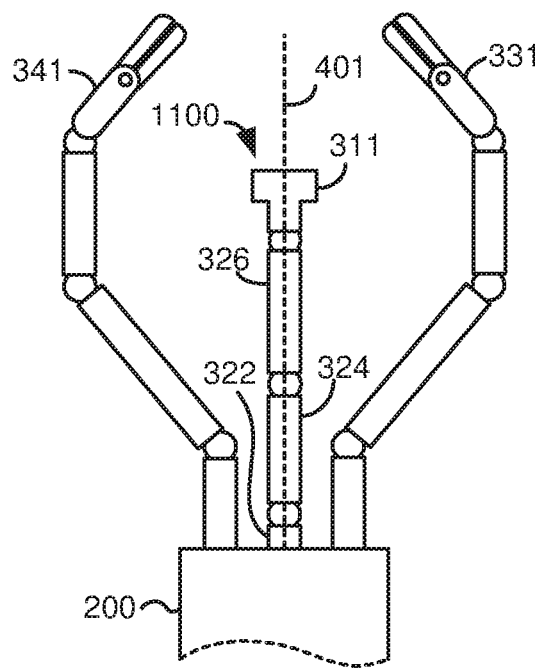
FIGS. 11-12 respectively illustrate top and right side views of a distal end of an entry guide with an articulated camera instrument in a preferred pose as used in a medical robotic system utilizing aspects of the present invention.
Figure 12:
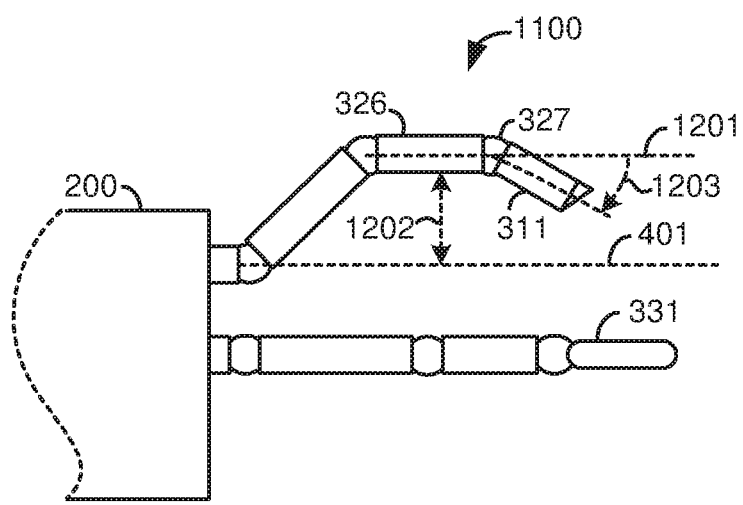

The preferred pose vector ($\hat{X}_{PP}$) provided by the camera pose selector block 1051 may be selected by the Surgeon or selected by default. FIGS. 11-12 respectively illustrate top and side views of an "optimal pose" for the camera instrument 211, which is preferably used as the default pose for the camera instrument 211. Looking downward at the optimal pose, as shown in FIG. 11, all links 322, 324, 326 of the camera instrument 211 are centered along the longitudinal axis 401 of the first link 322 so that they have maximum available range of lateral motion and provide a reference for the main insertion direction of the camera instrument 211. Further, the joggle joints 323, 325 are "joggled up", as shown in FIG. 12, so that the third link 326 is displaced a distance 1202 above the longitudinal axis 401 and the wrist assembly 327 is rotated at a negative pitch angle so that the camera tip 311 is oriented downwards at an angle 1203 so that the camera is preferably viewing the center of a workspace for the end effectors 331 and 341 of tool instruments 231 and 241, which are also extending out of the distal end of the entry guide 200 at the time. In this case, the operator is preferably allowed to freely move the camera 211 forward and backward in the input/output (I/O) direction so that the camera 211 may better view the end effectors 331, 341 as they move away from and back towards the distal end of the entry guide 200 during their use. Therefore, the setpoint generator block 1050 may use for such purpose the output 1041 of the forward kinematics block 1006 to modify the preferred pose vector ($\hat{X}_{PP}$) and guarantee that it "tracks" the operator commanded I/O movement of the camera 211.

Rather than strictly relying on the preferred pose ($\hat{X}_{PP}$) being selected by default, the Surgeon may also be provided with the capability to select the preferred pose by interacting through the pose selector block 1051. For example, the pose selector block 1051 may be implemented by the GUI 170, with a menu of instrument poses displayed on the monitor 104, one of which may be the default pose described above. The Surgeon may alternatively or additionally be provided with the capability to designate a current pose of the camera instrument 211 as the preferred pose in a number of ways such as depressing a button on the input device 108, providing a voice command understood by the voice recognition system 160, or stepping on the foot pedal 105 while the camera pose selector block 1051 is expecting an indication of such designation by the operator. The current pose is then stored in a memory as the preferred pose. As another way that the Surgeon may designate a current pose of the camera instrument 211 as the preferred pose, the Surgeon may use a computer mouse to click on a clickable icon displayed on the monitor 104 so that the current pose is stored in a memory as the preferred pose.

Figure 13:
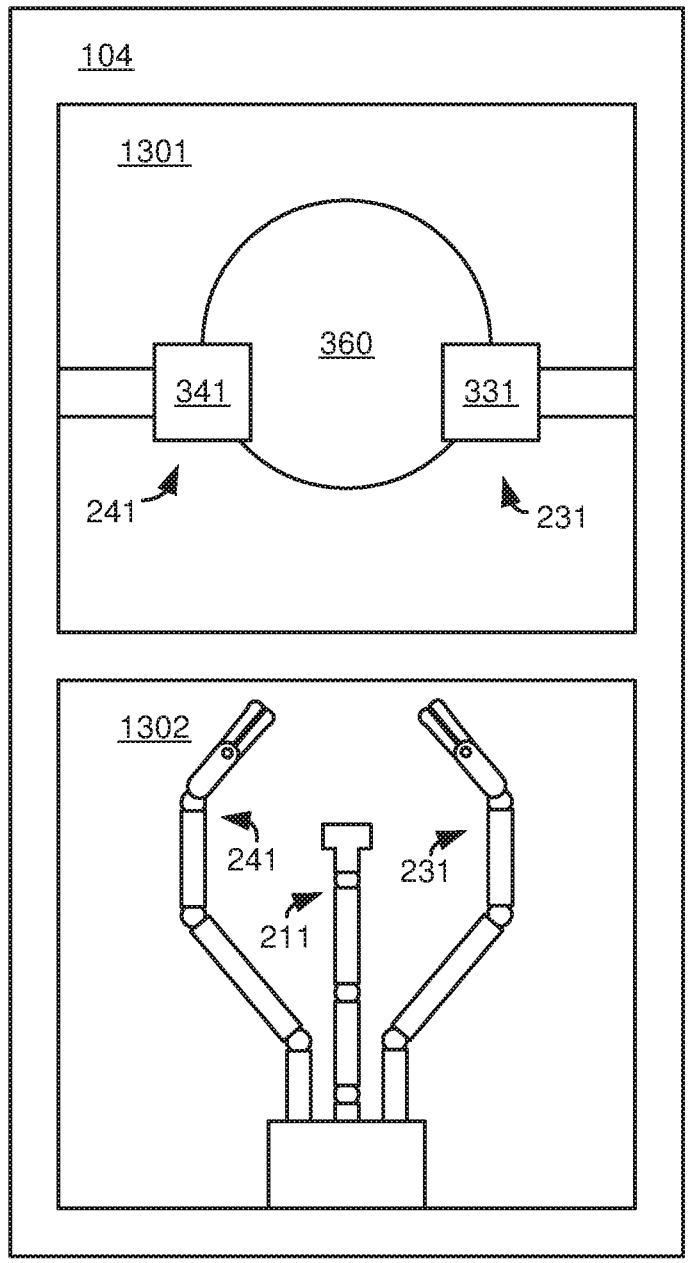
FIG. 13 illustrates an auxiliary view displayed adjacent to an image captured by the articulated camera instrument on a display screen in a medical robotic system utilizing aspects of the present invention.

To assist the Surgeon in deciding whether to designate the current pose of the camera instrument 211 as the preferred pose, an auxiliary view indicating the current configuration of the camera instrument 211 may be helpful. For example, FIG. 13 illustrates a view 1301 of a surgical site captured by the camera 211 and a corresponding auxiliary view 1302 generated by the processor 102 (using sensed position information for joints of the instrument 211 and entry guide 200) to indicate the current configuration of the camera instrument 211, as well as those of the tool instruments 231, 241, extending out of the distal end of the entry guide 200. As can be seen from the captured view 1301, very little information is provided for the positions of the non-seen joints and links of the instrument, whereas in the auxiliary view 1302, not only is information for the positions of the instrument's joints and links available, their respective positions relative to those of the other instruments 231, 241 are also available. For details on the generation of such computer generated auxiliary views, see, e.g., U.S. Pub. Applic. No. 2009/0326553 "Medical Robotic System Providing an Auxiliary View of Articulatable Instruments Extending out of a Distal End of an Entry Guide," which is incorporated herein by this reference. Although FIG. 13 shows both the captured image 1301 and the auxiliary view 1302 being displayed on the monitor 104, the auxiliary view 1302 may be viewed instead on a separate auxiliary display (not shown).

Figure 14:
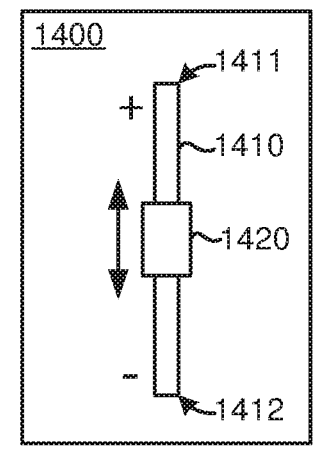
FIG. 14 illustrates a user interactive, graphical sliding control for adjusting a weighting used to calculate a setpoint for controlling movement of an articulated instrument in a medical robotic system utilizing aspects of the present invention.

In addition to specifying the preferred pose ($\hat{X}_{PP}$) through the camera pose selector block 1051, the Surgeon may also specify the weighting for each of the state variables used for calculating the setpoint in equation (1) using the stiffness selector block 1052. For example, the value for each weighting may be selected by the Surgeon interacting through the stiffness selector block 1052 with a corresponding graphical indicator displayed on the monitor 104, such as the user interactive, graphical slide control 1400 shown in FIG. 14. Using the graphical slide control 1400, any value for a weighting "$w_i$" between a maximum of "1" and a minimum of "0" may be selected by the Surgeon by placing a cursor on a graphical slide 1420 and causing the graphical slide 1420 to move up towards the top limit 1411 or down towards the bottom limit 1412 of a graphical scale 1410 while depressing a button on a mouse controlling movement of the cursor. Thus, separate weights may be defined by the Surgeon for each state variable so as to suit the Surgeon's personal preferences. A user selectable icon may also be provided for convenience on the monitor 104 by the stiffness selector block 1052, which when selected by the Surgeon sets all weights to "0" so as to allow the Surgeon to disable the centering behavior. Another user selectable icon may also be provided for convenience on the monitor 104 which when selected by the Surgeon sets all weights to "1" so as to effectively lock the camera instrument 211 in the preferred pose ($\hat{X}_{PP}$). It is important to note, however, that as long as the selected weighting is less than "1", the Surgeon is able to over-power any restoring force felt at the input device 108 as a result of such weighting and drive the camera to a desired position away from the preferred pose. Thus, the Surgeon still has full control over the motion of the camera instrument 211 in such case.

A simulated camera manipulator block 1004 transforms the setpoint vector ($\hat{X}_{SP}$) received on the output 1057 of the setpoint generator 1050 from the Cartesian space of the camera instrument 211 to its joint space using its inverse kinematics while avoiding singularities in its operation, limiting the commanded joint positions and velocities to avoid physical limitations or other constraints such as avoiding harmful contact with tissue or other parts of the Patient, and applying virtual constraints that may be defined to improve the performance of a medical procedure being performed at the time by the Surgeon using the medical robotic system 100.

The output 1024 of the simulated camera manipulator block 1004 is provided to a joint controller block 1005 and a forward kinematics block 1006. The joint controller block 1005 includes a joint control system for each controlled joint (or operatively coupled joints such as "joggle joints") of the camera instrument 211. The output 1024 of the simulated camera manipulator block 1004 provides the commanded value for each joint of the camera instrument 211. For feedback control purposes, sensors associated with each of the controlled joints of the camera instrument 211 provide sensor data 1032 back to the joint controller block 1005 indicating the current position and/or velocity of each joint of the camera instrument 211. The sensors may sense this joint information either directly (e.g., from the joint on the camera instrument 211) or indirectly (e.g., from the actuator in the camera manipulator 212 driving the joint). Each joint control system in the joint controller 1005 then generates torque commands for its respective actuator in the camera manipulator 212 so as to drive the difference between the commanded and sensed joint values to zero in a conventional feedback control system manner.

The forward kinematics block 1006 transforms the output 1024 of the simulated camera manipulator block 1004 from joint space back to Cartesian space relative to the eye reference frame using the forward kinematics of the camera instrument 211. The output 1041 of the forward kinematics block 1006 is provided to the scale and offset processing block 1001 as well as the simulated camera manipulator block 1004 for its internal computational purposes and the setpoint generator block 1050 for modifying the preferred pose vector ($\hat{X}_{PP}$) and/or weightings ($w_i$, i=1 . . . n) as previously described or otherwise as appropriate.

The scale and offset processing block 1001 performs inverse scale and offset functions on the output 1041 of the forward kinematics block 1006 before passing its output 1012 to the input processing block 1010 where an error value is calculated between its output 1011 and input 1012. If no limitation or other constraint had been imposed on the input 1021 to the simulated camera manipulator block 1004, then the calculated error value would be zero. On the other hand, if a limitation or constraint had been imposed, then the error value is not zero and it is converted to a torque command 1032 that drives actuators in the input device 108 to provide force feedback felt by the hands of the Surgeon. Thus, the Surgeon becomes aware that a limitation or constraint is being imposed by the force that he or she feels resisting his or her movement of the input device 108 in that direction.

In the present case, since the setpoint generator 1050 commands the simulated camera manipulator block 1004 to be driven to the setpoint vector ($\hat{X}_{SP}$) rather than the commanded state vector ($\hat{X}_{DES}$), an error value is calculated by the input processing block 1010 between its output 1011 and input 1012. As a result, the Surgeon perceives a spring-type force feedback on the input device 108 whenever the Surgeon is commanding the camera instrument 211 away from the preferred pose ($\hat{X}_{PP}$). The force feedback in this case is actually a vector of forces and torques, each applied in a different degree-of-freedom of the input device 108. In particular, since there is a direct relationship between translational and orientational movement of the input device and the commanded translational and orientational movement of the camera 211 in the system 100, as previously described, the weightings ($w_i$, i=1 . . . n) applied by the setpoint generator 1050 also serve to determine the magnitudes of the force feedback in each of the translational and orientational directions in the form of forces and torques felt by the Surgeon on the input device 108. Thus, heavier weighted state variables that refer to translational movement of the input device 108 and camera 211 result in higher force feedback gains felt on the input device 108 as resisting translational movement away from the preferred pose ($\hat{X}_{PP}$) and heavier weighted state variables that refer to orientational movement of the input device 108 and camera 211 result in higher torque feedback gains felt on the input device 108 as resisting orientational movement away from the preferred pose ($\hat{X}_{PP}$). To ensure that excessive friction in the input device 108 does not "overshadow" the "nudging" force felt on the input device 108, conventional friction and stiction compensation techniques may be used.

In addition, a non-linear characteristic may be used for the restoring force and torque, in order to modulate the stiffness as a function of the distance from the preferred pose and possibly of the velocity. For example, a deadband characteristic may be provided so that unconstrained operator commanded motion is allowed "nearby" the preferred pose ($\hat{X}_{PP}$) (i.e., no restoring force/toque feedback is applied within a threshold distance from the preferred pose) and the restoring force/torque is only felt beyond the threshold distance. At the threshold distance, the restoring force/torque feedback may or may not be applied as determined by default or operator selection.

Although the preferred pose mechanism described in reference to FIG. 10 above may be particularly useful in controlling movement of a bundled camera such as the camera instrument 211, it may also be useful in controlling movement of a bundled tool such as the tool instruments 231, 241 and/or controlling movement of an entry guide in which the bundled instruments are guided to a surgical site within a patient. For example, a preferred pose for one of the tool instruments 231, 241 may be a pose wherein its links are all aligned (i.e., the longitudinal axes of the links are aligned so that they coincide with each other). This pose would be useful during the retraction of the tool instrument back into the entry guide 200, for example. A preferred pose for the entry guide 200, on the other hand, may be one in which it points towards a target site in the patient or one in which a wide range of motion is provided for each of the tool instruments extending out of its distal end.

Although the various aspects of the present invention have been described with respect to a preferred embodiment, it will be understood that the invention is entitled to full protection within the full scope of the appended claims.

What is claimed is:

1. A method for controlling movement of a medical device, the method comprising:
    receiving, at a processor, a commanded state of a medical device from an input device;
    receiving, at the processor, a preferred pose of the medical device from a pose selector, the preferred pose being different, at a time of pose selection, than the commanded state and a current pose of the medical device, the preferred pose being one of a default pose and an operator defined pose, the default pose fixed for the medical device, the operator defined pose having been defined by an operator of the input device; and
    the processor:
        controlling movement of the medical device from the current pose of the medical device in response to the commanded state, and
        commanding a biasing force to be applied to the input device such that the biasing force increases when a difference between the commanded state and the preferred pose increases.

2. The method according to claim 1, wherein the processor commands the biasing force to be applied to the input device so as to indicate a weighted difference between the commanded state and the preferred pose.

3. The method according to claim 2, further comprising:
    receiving, at the processor, weighting coefficients to be used by the processor for commanding the biasing force to be applied to the input device so as to indicate the weighted difference between the commanded state and the preferred pose.

4. The method according to claim 3, wherein the weighting coefficients are received by processor from a stiffness selector which is configured to enable the operator of the input device to disable the biasing force to be applied to the input device by providing all weighting coefficients as zero values.

5. The method according to claim 3, wherein the weighting coefficients are received by processor from a stiffness selector which is configured to enable the operator of the input device to effectively lock the medical device in the preferred pose by providing all weighting coefficients as one values.

6. The method according to claim 3, wherein the weighting coefficients are received by processor from a stiffness selector which is operative by the operator of the input device so as to allow the operator to select one or more of the weighting coefficients to be used by the processor for commanding the biasing force to be applied to the input device so as to indicate the weighted difference between the commanded state and the preferred pose.

7. The method according to claim 1, further comprising:
    the processor:
        commanding an adjustment to the biasing force to be applied to the input device so as to indicate a difference between the commanded state and a modified preferred pose, the modified preferred pose determined by tracking movement of the medical device in an allowable direction relative to the preferred pose.

8. The method according to claim 1,
    wherein the operator defined pose corresponds to a prior pose of the medical device which was designated by the operator of the input device to be the preferred pose of the medical device.

9. The method according to claim 1,
    wherein the processor commands the biasing force to be applied to the input device so that the biasing force provides a spring-type force feedback on the input device when the input device is generating a commanded state that is different than the preferred pose.

10. The method according to claim 1,
    wherein the processor commands the biasing force to be applied to the input device so that the biasing force urges the operator of the input device to move the input device so as to command the medical device to be moved to the preferred pose.

11. The method according to claim 1,
    wherein the processor commands the biasing force to be applied to the input device so that the biasing force comprises a restoring force and a restoring torque, the restoring force being exerted against translational movement of the input device that commands the medical device away from the preferred pose, the restoring torque being exerted against rotational movement of the input device that commands the medical device away from the preferred pose.

12. The method according to claim 11, wherein the processor commands the biasing force to be applied to the input device so that at least one of the restoring force and the restoring torque is generated according to a spring function.

13. The method according to claim 12, wherein the spring function is characterized by a deadband so that the processor does not command a biasing force to be applied to the input device so as to indicate a difference between the commanded state and the preferred pose when the commanded state is within a threshold distance of the preferred pose.

14. The method according to claim 12, wherein the spring function is characterized by friction compensation.

15. The method according to claim 12, wherein the spring function is non-linear.

16. A method for controlling movement of a medical device, the method comprising:
receiving, at a processor, a commanded state of a medical device from an input device;
receiving, at the processor, a preferred pose of the medical device from a pose selector, the preferred pose being different, at a time of pose selection, than the commanded state and a current pose of the medical device, the preferred pose being one of a default pose and an operator defined pose, the default pose fixed for the medical device, the operator defined pose having been defined by an operator of the input device; and
the processor:
generating a modified commanded state by modifying the commanded state to accommodate a virtual constraint on movement of the medical device;
controlling movement of the medical device from the current pose of the medical device in response to the modified commanded state, and
commanding a biasing force to be applied to the input device such that the biasing force increases when a difference between the modified commanded state and the preferred pose increases.

17. The method according to claim 16, further comprising:
the processor:
commanding an adjustment to the biasing force to be applied to the input device so as to indicate a difference between the modified commanded state and a modified preferred pose, the modified preferred pose determined by tracking movement of the medical device in an allowable direction relative to the preferred pose.

18. The method according to claim 16, wherein the processor commands the biasing force to be applied to the input device so that the biasing force urges the operator of the input device to move the input device so as to command the medical device to be moved to the preferred pose.

19. A method for controlling movement of a medical device, the method comprising:
receiving, at a processor, a commanded state of a medical device from an input device;
receiving, at the processor, a preferred pose of the medical device from a pose selector, the preferred pose being different, at a time of pose selection, than the commanded state and a current pose of the medical device, the preferred pose being one of a default pose and an operator defined pose, the default pose fixed for the medical device, the operator defined pose having been defined by an operator of the input device; and
the processor:
generating a modified commanded state by modifying the commanded state to accommodate a physical constraint on movement of the medical device;
controlling movement of the medical device from the current pose of the medical device in response to the modified commanded state, and
commanding a biasing force to be applied to the input device such that the biasing force increases when a difference between the modified commanded state and the preferred pose increases.

20. The method according to claim 19, wherein the processor commands the biasing force to be applied to the input device so that the biasing force urges the operator of the input device to move the input device so as to command the medical device to be moved to the preferred pose.

* * * * *